United States Patent
Cooper et al.

(10) Patent No.: US 8,790,243 B2
(45) Date of Patent: Jul. 29, 2014

(54) FLEXIBLE WRIST FOR SURGICAL TOOL

(75) Inventors: Thomas G. Cooper, Menlo Park, CA (US); S. Christopher Anderson, San Francisco, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 258 days.

(21) Appl. No.: 13/020,625

(22) Filed: Feb. 3, 2011

(65) Prior Publication Data

US 2011/0125166 A1   May 26, 2011

Related U.S. Application Data

(60) Division of application No. 12/948,641, filed on Nov. 17, 2010, now Pat. No. 8,337,521, which is a continuation of application No. 11/733,879, filed on Apr. 11, 2007, now Pat. No. 7,862,580, which is a continuation of application No. 10/726,795, filed on Dec. 2, 2003, now Pat. No. 7,320,700.

(60) Provisional application No. 60/431,636, filed on Dec. 6, 2002.

(51) Int. Cl.
*A61B 1/00* (2006.01)

(52) U.S. Cl.
USPC ............................. 600/101; 606/205

(58) Field of Classification Search
USPC ................ 606/1, 205, 206; 600/101, 102
See application file for complete search history.

(56) References Cited

U.S. PATENT DOCUMENTS

| 1,418,184 | A | 5/1922 | Trunick |
| 2,815,697 | A | 12/1957 | Saunders-Singer |
| 2,901,258 | A | 8/1959 | Brandafi |

(Continued)

FOREIGN PATENT DOCUMENTS

| CH | 482439 | 12/1969 |
| DE | 1766809 B1 | 5/1972 |

(Continued)

OTHER PUBLICATIONS

Rosheim, Mark E., "Robot Wrist Actuators, 1995," pp. 95-206, A Wiley-Interscience Publication.

(Continued)

*Primary Examiner* — Victor Nguyen

(57) ABSTRACT

The present invention is directed to a tool having a wrist mechanism that provides pitch and yaw rotation in such a way that the tool has no singularity in roll, pitch, and yaw. In one embodiment, a minimally invasive surgical instrument includes an elongate shaft having a working end, a proximal end, and a shaft axis between the working end and the proximal end; and an end effector. A wrist member has a flexible tube including an axis extending through an interior surrounded by a wall. The wall of the flexible tube includes a plurality of lumens oriented generally parallel to the axis of the flexible tube. The wrist member has a proximal portion connected to the working end of the elongate shaft and a distal portion connected to the end effector. A plurality of actuation cables have distal portions connected to the end effector and extend from the distal portion through the lumens of the wall of the wrist member toward the elongate shaft to proximal portions which are actuatable to bend the wrist member in pitch rotation and yaw rotation.

18 Claims, 11 Drawing Sheets

(56) References Cited

U.S. PATENT DOCUMENTS

| | | |
|---|---|---|
| 3,145,333 A | 8/1964 | Pardini et al. |
| 3,190,286 A | 6/1965 | Stokes |
| 3,266,059 A | 8/1966 | Stelle |
| 3,268,059 A | 8/1966 | Hill |
| 3,463,329 A | 8/1969 | Gartner |
| 3,628,535 A | 12/1971 | Ostrowsky et al. |
| 3,788,303 A | 1/1974 | Hall |
| 3,818,125 A | 6/1974 | Butterfield |
| 3,921,445 A | 11/1975 | Hill et al. |
| 3,923,166 A | 12/1975 | Fletcher et al. |
| 3,934,201 A | 1/1976 | Majefski |
| 4,038,987 A | 8/1977 | Komiya |
| 4,113,115 A | 9/1978 | Yoshio |
| 4,149,278 A | 4/1979 | Frosch et al. |
| 4,150,326 A | 4/1979 | Engelberger et al. |
| 4,203,430 A | 5/1980 | Takahashi |
| 4,260,319 A | 4/1981 | Motoda et al. |
| 4,264,266 A | 4/1981 | Trechsel |
| 4,281,447 A | 8/1981 | Miller et al. |
| 4,329,980 A | 5/1982 | Terada |
| 4,332,066 A | 6/1982 | Hailey et al. |
| 4,349,837 A | 9/1982 | Hinds |
| 4,367,998 A | 1/1983 | Causer |
| 4,419,041 A | 12/1983 | Rose |
| 4,483,326 A | 11/1984 | Yamaka et al. |
| 4,486,928 A | 12/1984 | Tucker et al. |
| 4,500,065 A | 2/1985 | Hennekes et al. |
| 4,510,574 A | 4/1985 | Guittet et al. |
| 4,511,305 A | 4/1985 | Kawai et al. |
| 4,512,709 A | 4/1985 | Hennekes et al. |
| 4,562,463 A | 12/1985 | Lipton |
| 4,580,551 A | 4/1986 | Carpenter et al. |
| 4,582,067 A | 4/1986 | Silverstein et al. |
| 4,583,117 A | 4/1986 | Lipton et al. |
| 4,611,888 A | 9/1986 | Prenovitz et al. |
| 4,622,954 A | 11/1986 | Arakawa et al. |
| 4,636,138 A | 1/1987 | Gorman |
| 4,651,201 A | 3/1987 | Schoolman |
| 4,697,577 A | 10/1987 | Forkner |
| 4,706,372 A | 11/1987 | Ferrero et al. |
| 4,708,434 A | 11/1987 | Tsuno |
| 4,710,093 A | 12/1987 | Zimmer et al. |
| 4,722,056 A | 1/1988 | Roberts et al. |
| 4,726,355 A | 2/1988 | Okada |
| 4,744,363 A | 5/1988 | Hasson |
| 4,750,475 A | 6/1988 | Yoshihashi |
| 4,751,925 A | 6/1988 | Tontarra |
| 4,762,455 A | 8/1988 | Coughlan et al. |
| 4,766,775 A | 8/1988 | Hodge |
| 4,793,053 A | 12/1988 | Zuccaro et al. |
| 4,806,068 A | 2/1989 | Kohli et al. |
| 4,808,898 A | 2/1989 | Pearson |
| 4,809,747 A | 3/1989 | Choly et al. |
| 4,830,569 A | 5/1989 | Jannborg |
| 4,832,198 A | 5/1989 | Alikhan |
| 4,833,383 A | 5/1989 | Skarr et al. |
| 4,834,069 A | 5/1989 | Umeda |
| 4,837,703 A | 6/1989 | Kakazu et al. |
| 4,837,734 A | 6/1989 | Ichikawa et al. |
| 4,853,874 A | 8/1989 | Iwamoto et al. |
| 4,855,822 A | 8/1989 | Narendra et al. |
| 4,860,215 A | 8/1989 | Seraji |
| 4,862,873 A | 9/1989 | Yajima et al. |
| 4,863,133 A | 9/1989 | Bonnell |
| 4,873,572 A | 10/1989 | Miyazaki et al. |
| 4,899,730 A | 2/1990 | Stennert et al. |
| 4,919,112 A | 4/1990 | Siegmund |
| 4,919,382 A | 4/1990 | Forman |
| 4,922,338 A | 5/1990 | Arpino |
| 4,928,546 A | 5/1990 | Walters |
| 4,941,106 A | 7/1990 | Krieger |
| 4,942,538 A | 7/1990 | Yuan et al. |
| 4,942,539 A | 7/1990 | McGee et al. |
| 4,943,939 A | 7/1990 | Hoover |
| 4,947,702 A | 8/1990 | Kato |
| 4,979,496 A | 12/1990 | Komi |
| 4,979,949 A | 12/1990 | Matsen, III et al. |
| 4,989,253 A | 1/1991 | Liang et al. |
| 4,996,975 A | 3/1991 | Nakamura |
| 5,002,418 A | 3/1991 | McCown et al. |
| 5,018,266 A | 5/1991 | Hutchinson et al. |
| 5,020,933 A | 6/1991 | Salvestro et al. |
| 5,029,574 A | 7/1991 | Shimamura et al. |
| 5,045,936 A | 9/1991 | Lobb et al. |
| 5,046,022 A | 9/1991 | Conway et al. |
| 5,053,687 A | 10/1991 | Merlet |
| 5,060,532 A | 10/1991 | Barker |
| 5,062,761 A | 11/1991 | Glachet |
| 5,078,140 A | 1/1992 | Kwoh |
| 5,096,236 A | 3/1992 | Thony |
| 5,141,519 A | 8/1992 | Smith et al. |
| 5,142,930 A | 9/1992 | Allen et al. |
| 5,143,453 A | 9/1992 | Weynant Nee Girones |
| 5,154,717 A | 10/1992 | Matsen, III et al. |
| 5,174,300 A | 12/1992 | Bales et al. |
| 5,179,935 A | 1/1993 | Miyagi |
| 5,182,641 A | 1/1993 | Diner et al. |
| 5,184,601 A | 2/1993 | Putman |
| 5,187,796 A | 2/1993 | Wang et al. |
| 5,209,747 A | 5/1993 | Knoepfler |
| 5,217,003 A | 6/1993 | Wilk |
| 5,219,351 A | 6/1993 | Teubner et al. |
| 5,221,283 A | 6/1993 | Chang |
| 5,236,432 A | 8/1993 | Matsen, III et al. |
| 5,239,883 A | 8/1993 | Rosheim |
| 5,253,706 A | 10/1993 | Reid |
| 5,254,130 A | 10/1993 | Poncet et al. |
| 5,255,429 A | 10/1993 | Nishi et al. |
| 5,257,998 A | 11/1993 | Ota et al. |
| 5,260,319 A | 11/1993 | Effland et al. |
| 5,264,266 A | 11/1993 | Yokoyama et al. |
| 5,271,384 A | 12/1993 | McEwen et al. |
| 5,273,039 A | 12/1993 | Fujiwara et al. |
| 5,279,309 A | 1/1994 | Taylor et al. |
| 5,281,220 A | 1/1994 | Blake, III |
| 5,284,130 A | 2/1994 | Ratliff |
| 5,294,209 A | 3/1994 | Naka et al. |
| 5,299,288 A | 3/1994 | Glassman et al. |
| 5,299,559 A | 4/1994 | Bruce et al. |
| 5,305,203 A | 4/1994 | Raab |
| 5,312,212 A | 5/1994 | Naumec |
| 5,313,306 A | 5/1994 | Kuban et al. |
| 5,313,935 A | 5/1994 | Kortenbach et al. |
| 5,321,353 A | 6/1994 | Furness |
| 5,325,866 A | 7/1994 | Krzyzanowski |
| 5,325,886 A | 7/1994 | Klink |
| 5,339,799 A | 8/1994 | Kami et al. |
| 5,341,950 A | 8/1994 | Sinz |
| 5,343,385 A | 8/1994 | Joskowicz et al. |
| 5,351,676 A | 10/1994 | Putman |
| 5,354,314 A | 10/1994 | Hardy et al. |
| 5,355,743 A | 10/1994 | Tesar |
| 5,359,993 A | 11/1994 | Slater et al. |
| 5,368,015 A | 11/1994 | Wilk |
| 5,372,147 A | 12/1994 | Lathrop, Jr. et al. |
| 5,382,885 A | 1/1995 | Salcudean et al. |
| 5,383,888 A | 1/1995 | Zvenyatsky et al. |
| 5,397,323 A | 3/1995 | Taylor et al. |
| 5,399,951 A | 3/1995 | Lavallee et al. |
| 5,400,267 A | 3/1995 | Denen et al. |
| 5,402,801 A | 4/1995 | Taylor |
| 5,403,319 A | 4/1995 | Matsen, III et al. |
| 5,410,944 A | 5/1995 | Cushman |
| 5,417,210 A | 5/1995 | Funda et al. |
| 5,423,648 A | 6/1995 | Akeel et al. |
| 5,425,528 A | 6/1995 | Rains et al. |
| 5,427,097 A | 6/1995 | Depp |
| 5,430,643 A | 7/1995 | Seraji |
| 5,441,505 A | 8/1995 | Nakamura |
| 5,448,989 A | 9/1995 | Heckele |
| 5,451,368 A | 9/1995 | Jacob |
| 5,454,827 A | 10/1995 | Aust et al. |
| 5,460,168 A | 10/1995 | Masubuchi et al. |
| 5,474,566 A | 12/1995 | Alesi et al. |

(56) References Cited

U.S. PATENT DOCUMENTS

| | | |
|---|---|---|
| 5,474,571 A | 12/1995 | Lang |
| 5,479,930 A | 1/1996 | Gruner et al. |
| 5,480,409 A | 1/1996 | Riza |
| 5,499,320 A | 3/1996 | Backes et al. |
| 5,503,320 A | 4/1996 | Webster et al. |
| 5,503,616 A | 4/1996 | Jones |
| 5,515,478 A | 5/1996 | Wang |
| 5,520,678 A | 5/1996 | Heckele et al. |
| 5,524,180 A | 6/1996 | Wang et al. |
| 5,553,198 A | 9/1996 | Wang et al. |
| 5,577,991 A | 11/1996 | Akui et al. |
| 5,582,576 A | 12/1996 | Hori et al. |
| 5,611,813 A | 3/1997 | Lichtman |
| 5,618,294 A | 4/1997 | Aust et al. |
| 5,624,398 A | 4/1997 | Smith et al. |
| 5,625,576 A | 4/1997 | Massie et al. |
| 5,631,973 A | 5/1997 | Green |
| 5,636,138 A | 6/1997 | Gilbert et al. |
| 5,649,956 A | 7/1997 | Jensen et al. |
| 5,657,429 A | 8/1997 | Wang et al. |
| 5,695,500 A | 12/1997 | Taylor et al. |
| 5,697,939 A | 12/1997 | Kubota et al. |
| 5,699,695 A | 12/1997 | Canfield et al. |
| 5,715,729 A | 2/1998 | Toyama et al. |
| 5,737,500 A | 4/1998 | Seraji et al. |
| 5,740,699 A | 4/1998 | Ballantyne et al. |
| 5,748,767 A | 5/1998 | Raab |
| 5,754,741 A | 5/1998 | Wang et al. |
| 5,755,731 A | 5/1998 | Grinberg |
| 5,762,458 A | 6/1998 | Wang et al. |
| 5,776,049 A | 7/1998 | Takahashi |
| 5,784,542 A | 7/1998 | Ohm et al. |
| 5,791,231 A | 8/1998 | Cohn et al. |
| 5,792,135 A | 8/1998 | Madhani et al. |
| 5,797,900 A | 8/1998 | Madhani et al. |
| 5,800,423 A | 9/1998 | Jensen |
| 5,808,665 A | 9/1998 | Green |
| 5,810,715 A | 9/1998 | Moriyama |
| 5,810,880 A | 9/1998 | Jensen et al. |
| 5,814,038 A | 9/1998 | Jensen et al. |
| 5,815,640 A | 9/1998 | Wang et al. |
| 5,820,545 A | 10/1998 | Arbter et al. |
| 5,855,553 A | 1/1999 | Tajima et al. |
| 5,855,583 A | 1/1999 | Wang et al. |
| 5,859,934 A | 1/1999 | Green |
| 5,860,912 A | 1/1999 | Chiba |
| 5,864,359 A | 1/1999 | Kazakevich |
| 5,868,760 A | 2/1999 | McGuckin, Jr. |
| 5,876,325 A | 3/1999 | Mizuno et al. |
| 5,878,193 A | 3/1999 | Wang et al. |
| 5,885,288 A | 3/1999 | Aust et al. |
| 5,907,664 A | 5/1999 | Wang et al. |
| 5,908,436 A | 6/1999 | Cuschieri et al. |
| 5,911,036 A | 6/1999 | Wright et al. |
| 5,916,146 A | 6/1999 | Allotta et al. |
| 5,931,832 A | 8/1999 | Jensen |
| 5,938,678 A | 8/1999 | Zirps et al. |
| 5,960,125 A | 9/1999 | Michael et al. |
| 5,971,976 A | 10/1999 | Wang et al. |
| 6,053,907 A | 4/2000 | Zirps |
| 6,071,233 A | 6/2000 | Ishikawa et al. |
| 6,077,287 A | 6/2000 | Taylor et al. |
| 6,116,802 A | 9/2000 | Gueret |
| 6,120,433 A | 9/2000 | Mizuno et al. |
| 6,132,368 A | 10/2000 | Cooper |
| 6,174,280 B1 | 1/2001 | Oneda et al. |
| 6,191,809 B1 | 2/2001 | Hori et al. |
| 6,196,081 B1 | 3/2001 | Yau |
| 6,244,809 B1 | 6/2001 | Wang et al. |
| 6,270,453 B1 | 8/2001 | Sakai |
| 6,296,635 B1 * | 10/2001 | Smith et al. ............ 606/19 |
| 6,306,081 B1 | 10/2001 | Ishikawa et al. |
| 6,307,285 B1 | 10/2001 | Delson et al. |
| 6,312,435 B1 | 11/2001 | Wallace et al. |
| 6,330,837 B1 | 12/2001 | Charles et al. |
| 6,331,181 B1 | 12/2001 | Tierney et al. |
| 6,335,755 B1 | 1/2002 | McLaine et al. |
| 6,394,998 B1 | 5/2002 | Wallace et al. |
| 6,418,811 B1 | 7/2002 | Rosheim |
| 6,424,885 B1 | 7/2002 | Niemeyer et al. |
| 6,425,177 B1 | 7/2002 | Akeel |
| 6,436,107 B1 | 8/2002 | Wang et al. |
| 6,450,948 B1 | 9/2002 | Matsuura et al. |
| 6,451,027 B1 | 9/2002 | Cooper et al. |
| 6,471,637 B1 | 10/2002 | Green et al. |
| 6,491,701 B2 | 12/2002 | Tierney et al. |
| 6,516,681 B1 | 2/2003 | Pierrot et al. |
| 6,522,906 B1 | 2/2003 | Salisbury, Jr. et al. |
| 6,658,962 B1 | 12/2003 | Rosheim |
| 6,676,684 B1 | 1/2004 | Morley et al. |
| 6,699,235 B2 | 3/2004 | Wallace et al. |
| 6,743,239 B1 | 6/2004 | Kuehn et al. |
| 6,786,896 B1 | 9/2004 | Madhani et al. |
| 6,807,295 B1 | 10/2004 | Ono |
| 6,817,974 B2 | 11/2004 | Cooper et al. |
| 6,858,003 B2 | 2/2005 | Evans et al. |
| 7,066,926 B2 | 6/2006 | Wallace et al. |
| 7,273,488 B2 | 9/2007 | Nakamura et al. |
| 7,320,700 B2 | 1/2008 | Cooper et al. |
| 7,691,098 B2 | 4/2010 | Wallace et al. |
| 7,736,356 B2 | 6/2010 | Cooper et al. |
| 7,862,580 B2 | 1/2011 | Cooper et al. |
| 8,142,421 B2 | 3/2012 | Cooper et al. |
| 8,337,521 B2 | 12/2012 | Cooper et al. |
| 2001/0023313 A1 | 9/2001 | Ide |
| 2002/0045888 A1 * | 4/2002 | Ramans et al. ............ 606/1 |
| 2002/0103418 A1 | 8/2002 | Maeda et al. |
| 2002/0107530 A1 | 8/2002 | Sauer et al. |
| 2003/0028217 A1 | 2/2003 | Nakamura et al. |
| 2004/0158268 A1 | 8/2004 | Danitz et al. |
| 2004/0186345 A1 | 9/2004 | Yang et al. |
| 2004/0236316 A1 | 11/2004 | Danitz et al. |
| 2005/0182298 A1 | 8/2005 | Ikeda et al. |
| 2006/0178556 A1 | 8/2006 | Hasser et al. |
| 2006/0199999 A1 | 9/2006 | Ikeda et al. |
| 2011/0028991 A1 | 2/2011 | Ikeda et al. |
| 2012/0190920 A1 | 7/2012 | Hasser et al. |
| 2012/0220831 A1 | 8/2012 | Cooper et al. |
| 2013/0012928 A1 | 1/2013 | Cooper et al. |
| 2013/0096540 A1 | 4/2013 | Cooper et al. |

FOREIGN PATENT DOCUMENTS

| | | |
|---|---|---|
| DE | 2819976 | 11/1979 |
| DE | 3806190 | 9/1988 |
| DE | 4138861 | 10/1992 |
| DE | 4213426 | 10/1992 |
| DE | 4136861 | 5/1993 |
| DE | 4442185 A1 | 5/1996 |
| EP | 239409 | 9/1987 |
| EP | 0291292 | 11/1988 |
| EP | 0595291 | 5/1994 |
| EP | 1575439 B1 | 4/2012 |
| FR | 2460762 | 1/1981 |
| FR | 2593106 | 3/1990 |
| FR | 8600852 | 3/1990 |
| GB | 2040134 | 8/1980 |
| GB | 2117732 | 10/1983 |
| JP | H0538342 A | 2/1993 |
| JP | 5184525 | 7/1993 |
| JP | H05305052 A | 11/1993 |
| JP | H06285010 A | 10/1994 |
| JP | H08160315 A | 6/1996 |
| JP | H10258024 A | 9/1998 |
| JP | 2008531222 A | 8/2008 |
| JP | 2010099530 A | 5/2010 |
| WO | WO9216141 | 10/1992 |
| WO | WO9313916 | 7/1993 |
| WO | WO9426167 | 11/1994 |
| WO | WO9501757 | 1/1995 |
| WO | WO9516396 | 6/1995 |
| WO | WO9530964 | 11/1995 |
| WO | WO9639944 | 12/1996 |
| WO | WO-9723158 A1 | 7/1997 |

(56) References Cited

FOREIGN PATENT DOCUMENTS

| WO | WO-9740966 A1 | 11/1997 |
|---|---|---|
| WO | WO-9910137 A1 | 3/1999 |
| WO | WO9950721 | 10/1999 |
| WO | WO2004052171 A2 | 6/2004 |
| WO | WO2004052171 A3 | 6/2004 |
| WO | WO-2005099560 A1 | 10/2005 |
| WO | WO-2006094242 A1 | 9/2006 |

OTHER PUBLICATIONS

Adams, Ludwig et al., "Computer-Assisted Surgery," IEEE Computer Graphics & Applications, May 1990, pp. 43-52, vol. 10—Issue 3, IEEE Computer Society Press.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1973, pp. 121-136, vol. 2, Springer-Verlag.

Arai, Tatsuo et al., "Bilateral control for manipulators with different configurations," IECON Inn Conference on Industrial Electronics Control and Instrumentation, Oct. 22-26, 1984, pp. 40-45, vol. 1.

Asada Haruhiko et al., "Development of a direct drive arm using high torque brushless motors," Proc. of 1st Int. Symp. on Robotics Research, 1984, pp. 583-599, Chapter 7, MIT Press.

Baker, Daniel R. et al., "On the inverse kinematics of redundant manipulators," The International Journal of Robotics Research, Inc, Mar. 21, 1988, pp. 3-21, vol. 7—Issue 2, Sage Publications.

Bejczy, Antal K. et al., "Controlling Remote Manipulators through Kinesthetic Coupling," Computers in Mechanical Engineering, 1983, pp. 48-60, vol. 1—Issue 1.

Blue Cross, Another Pair of Hands for Surgeon, The Blue Cross magazine Perspective, 1972, 3 Pages Total.

Borovoi, A.V., "Stability of a manipulator with force feedback," Izv. AN SSSR Mekhanika Tverdogo Teal, 1990, pp. 37-45, vol. 25—Issue 1, Allerton Press, Inc.

Burdea, Grigore et al., "Dextrous Telerobotics with Force Feedback—an overview. Part 2: Control and Implementation," Robotica, 1991, pp. 291-298, vol. 9.

Caccavale, Fabrizio et al., "Experiments of kinematic control on a redundant robot manipulator with non-spherical wrist," Laboratory Robotics and Automation, 1996, pp. 25-36, vol. 8—Issue 1.

Chang, Kyong-Sok et al., "Manipulator control at kinematic singularities: A dynamically consistent strategy," IEEE International Conference on Robotics and Automation, 1995, pp. 84-88, vol. 3, IEEE.

Cohn, Michael C., "Medical Robotics," http://www-bsac.eecs.berkeley.edu/ , 1996, pp. 1-8 and 4.

Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.

Fisher, Scott S., "Virtual interface environment," IEEE/A1AA 7th Digital Avionics Systems Conference Ft. Worth Texas, 1986, pp. 346-350, IEEE.

Fu, K.S. et al., "Robotics: control, sensing, vision, and intelligence," 1987, pp. 12-265, Ch. 2 & 5, McGraw-Hill Book Company.

Fukuda, Toshio et al., "A new method of master-slave type of teleoperation for a micro-manipulator system," IEEE Microrobots and Teleoperations Workshop, 1987, 5 pages, IEEE.

Funda, Janez et al., "Constrained Cartesian Motion Control for Teleoperated Surgical Robots," IEEE Transactions on Robotics and Automation, IEEE, Jun. 1996, vol. 12, No. 3, pp. 453-465.

Furuta, Katsuhisa et al., "Master slave manipulator based on virtual internal model following control concept," IEEE Intl. Conference on Robotics and Automation, 1987, pp. 567-572, vol. 4, IEEE.

Green, Philip, S. et al., "Mobile telepresence surgery," 2nd Annual Intl Symposium on Med. Robotics and Computer Assisted Surgery, Maryland Nov. 1995, pp. 97-103.

Green, Philip S. et al., "Telepresence Surgery," IEEE Engineering in Medicine and Biology Magazine, May/Jun. 1995, pp. 324-329, vol. 14—Issue 3, IEEE.

Guerrouad, Aicha et al., "SMOS: Stereotaxical Microtelemanipulator for Ocular Surgery," IEEE Engineering in Medicine & Biology Society 11th annual international conference, Nov. 9-12, 1989, pp. 879-880, vol. 3, IEEE.

Hannaford, Blake et al., "Experimental and simulation studies of hard contact in force reflecting teleoperation," IEEE International Conference on Robotics and Automation Proceedings, 1998, pp. 584-589, vol. 1, IEEE.

Held, Richard et al., "Telepresence, Time Delay and Adaptation", *, Spatial Displays and Spatial Instruments Proceedings of a Conference sponsored by NASA Ames Research Center and the School of Optometry, Univ. of California, Aug. 31-Sep. 3, 1987, Published 1989, pp. 28-1 through 28-16.

Hill, John W., "Telepresence surgery demonstration system," Robotics and Automation, 1994, pp. 2302-2307, vol. 3, SRI International.

Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.

Inoue, Masao; "Six-Axis bilateral control of an articulated slave manipulator using a Cartesian master manipulator," Advanced robotics, 1990, pp. 139-150, vol. 4—Issue 2, Robotic society of Japan.

"Introduction to New Project for The National Research Development Program (Large-Scale Project) in FY 1991—Micromachine Technology", Agency of Industrial Science and Technology Ministry of International Trade and Industry, Japan, 1991, pp. 1-11.

Jau, B. M., "Anthropomorphic Remote Manipulator," NASA Tech Briefs, Apr. 1991, pp. 92, NASA's Jet Propulsion Laboratory, Pasadena, California.

Jones, Daniel B. et al., "Next generation 3D videosystems may improve laprascopic task performance," Interactive Technology and the New Paradigm for Healthcare, 1995, pp. 152-160, Ch 25.

Kazerooni H., "Design and analysis of the statically balanced direct-drive robot manipulator," Robotics and Computer-Integrated Manufacturing, 1989, pp. 287-293, vol. 6, Issue 4.

Kazerooni, H. et al., "The Dynamics and Control of a Haptic Interface Device," IEEE Transactions on Robotics and Automation, 1994, pp. 453-464, vol. 10—Issue 4, IEEE.

Kazerooni, H., "Human/Robot Interaction via the Transfer of Power and Information Signals Part I: Dynamics and Control Analysis," IEEE International Conference on Robotics and Automation, 1989, pp. 1632-1640, IEEE.

Khatib, Oussama, "Reduced effective inertia in macro / mini manipulator systems," Proceedings of ACC, 1988, pp. 2140-2147.

Kim, Won S. et al., "A Helmet Mounted Display for Telerobotics," Compcon Spring '88. Thirty-Third IEEE Computer Society International Conference, 1988, pp. 543-547, IEEE.

Kim, Won S. et al., "Active compliance and damping in telemanipulator control," Jet Propulsion Laboratory New technology Report, 1991, pp. 1-14a, vol. 15—Issue 4, JPL & NASA Case No. NP0-1796917466, Item 40.

Kosuge Kazuhiro, et al., "Unified Approach for Teleoperation of Virtual and Real Environment for Skill Based Teleoperation," Proceedings of the IEEE/RSJ/GI International Conference on Intelligent Robots and Systems, 1994, pp. 1242-1247, vol. 2, IEEE.

Kosuge, Kazuhiro et al., "Unified approach for teleoperation of virtual and real environment manipulation based on reference dynamics," IEEE International Conference on Robotics and Automation, 1995, pp. 938-943, IEEE.

Kwoh, Yik, San et al., "A Robot With Improved Absolute Positioning Accuracy for CT Guided Stereotactic Brain Surgery," IEEE Transactions on Biomedical Engineering, Feb. 1988, pp. 153-160, vol. 35—Issue 2, IEEE.

Madhani, Akhil J., "Design of Teleoperated Surgical Instruments for Minimally Invasive Surgery," Feb. 1998, pp. 1-251.

Madhani, Akhil J. et al., "The black falcon: A teleoperated surgical instrument for minimally invasive surgery," IEEE/RSJ Int. Conf. on Intelligent Robots and Systems (IROS) Victoria B.C. Canada ), 1998, pp. 936-944, vol. 2, IEEE.

(56) References Cited

OTHER PUBLICATIONS

Massie, Thomas H. et al., "The PHANTOM Haptic Interface: A Device for Probing Virtual Objects," Proceedings of the ASME Winter Annual Meeting, Symposium on Haptic Interfaces for Virtual Environment and Teleoperator Systems, 1994, pp. 7.
Matsushima, K. et al., "Servo Micro-Manipulator Tiny-Micro Mark-1," 4th Symposium on Theory and Practice of Robots and Manipulators, 1982, pp. 193-201.
Mitsuishi, Mamoru et al., "A tele-micro-surgery system with co-located view and operation points and a rotational-force-feedback-free master manipulator," 2nd Annual Intl. Symposium on Medical robotics and Computer Assisted Surgery Baltimore Maryland, Nov. 4-7, 1995, pp. 111-118.
Moyer, Thomas H., "The design for an integrated hand and wrist mechanism," Masters Thesis, Feb. 1992, pp. 1-106, Massachusetts Institute of Technology.
Neisius B. et al., "Entwicklung eines Manipulators zur endoskopischen Handhabung chirurgischer Effektoren," Nachrichten—Forschungszentrum Karlsruhe, 1995, pp. 173-180.
Neisius B. et al., "Robotic manipulator for endoscopic handling of surgical effectors and cameras," 1st Intl. Symposium on Medical Robotics and Computer Assisted Surgery, 1994, pp. 169-175, vol. 2.
Ng, W.S. et al., "Robotic Surgery, A First-Hand Experience in Transurethral Resection of the Prostate," IEEE Engineering in Medicine and Biology, Mar. 1993, pp. 120-125, vol. 12—Issue 1, IEEE.
PCT/US03/38462 International Search Report, mailed Feb. 18, 2005, 3 pages.
Richter, Ruthann, "Telesurgery may bridge future gaps," Times Tribune, Jan. 24, 1988, pp. A-1 and A-16.
Rosheim, Mark E., Chapter 5: "Pitch-Yaw-Roll Wrists," *Robot Wrist Actuators*, Wiley & Sons, New York, 1989, pp. 95-206.
Rosheim Mark E., "Robot Wrist Actuators", John Wiley & Sons, Inc., New York, 1989, pp. 112-114, Figures 5.23-5.26, p. 140, figure 5.54.
Rosheim, Mark E., *Robot Wrist Actuators*, Wiley & Sons, New York, 1989.
Salisbury, Kenneth J., "Kinematic and force analysis of articulated hands," Department of Computer Science Stanford University Report No. STAN CS 89 921, 1982, Chapter 9, pp. 67-77.
Sastry Shankar et al., "Millirobotics for remote minamally invasive surgery," Proceedings of the Intl. Workshop on Some Critical Issues in Robotics Singapore, Oct. 2-3, 1995, pp. 81-98.
Sastry, Shankar, "MilliRobotics in Minimally Invasive Telesurgery," Internet, http://robotics.eecs.berkeley.edu, 1996, pp. 8.
Spain, Edward H., "Stereo Advantage for a Peg in Hole Task Using a Force Feedback Manipulator," SPIE Stereoscopic Displays and Applications, 1990, pp. 244-254, vol. 1256, IEEE.
Tachi, Susumu et al., "Tele-Existence Master Slave System For Remote Manipulation (II)," IEEE Conference on Decision and Control Honolulu Hawaii, Dec. 5-7, 1990, pp. 85-90, vol. 1—Issue 6, IEEE.
Task 2: Miniature end effector—A preliminary design, pp. 32-47, no date.
Taubes, Gary et al., "Surgery in Cyberspace," Discover magazine, Dec. 1994, vol. 15, issue 12, pp. 85-92.
Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.
Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited.
Trevelyan, James P. et al., "Motion Control for a Sheep Shearing Robot," First Intl. Symposium Robotics Research, 1984, pp. 175-190, Chapter 2, MIT Press.
Trevelyan, James P. et al., "Motion Control for a Sheep Shearing Robot," IEEE Robotics Research Conference, the 1st International Symposium, Carroll, NH, USA., 1983, pp. 175-190, MIT Press.
Vertut, Jean and Phillipe Coiffet, *Robot Technology: Teleoperation and Robotics Evolution and Development*, English translation Prentice-Hall, Inc., Inglewood Cliffs, NJ, USA 1986, vol. 3A, 332 pages.
Vibet, C., "Properties of Master Slave Robots," Motor-con, 1987, pp. 309-316.
Wampler, Charles W. et al., "Wrist singularities: Theory and practice," The Robotics Review 2, 1992, pp. 173-189, MIT Press.
Wampler, Charles W. II et al., "An Implementation of Inverse Kinematic Functions for Control of a Redundant Wrist," Proc. IEEE International Conference on Robotics and Automation, 1989, pp. 914-919, vol. 14—Issue 19, IEEE.
Wampler, Charles W., "Inverse kinematic functions for redundant spherical wrists," IEEE Transactions on Robotics and Automation, 1989, pp. 106-111, vol. 5—Issue 1, IEEE.
Wampler, Charles W., "The Inverse Function Approach To Kinematic Control Of Redundant Manipulators," American Control Conference, 1982, pp. 1364-1369, vol. 25.
European Search Report for Application No. 11002838, mailed on Apr. 29, 2013, 6 pages.
Peirs J., et al., "A Flexible Distal Tip with Two Degrees of Freedom for Enhanced Dexterity in Endoscopic Robot Surgery," MME'02, The 13th Micromechanics Europe Workshop, Oct. 6-8, 2002, Sinaia, Romania, pp. 271-274.
Supplementary European Search Report for Application No. EP03790301, mailed on Jul. 2, 2009, 3 pages.
European Search Report for Application No. EP11002837 mailed on Apr. 25, 2013, 6 pages.
International Preliminary Examination Report for Application No. PCT/US02/20884, mailed on Jul. 13, 2004, 3 pages.
International Preliminary Examination Report for Application No. PCT/US02/20921, mailed on May 24, 2004, 4 pages.
International Search Report for application No. PCT/US02/20884, Mailed on May 8, 2003, 1 page.
International Search Report for application No. PCT/US02/20921, Mailed on Jun. 17, 2003, 1 page.
International Search Report for application No. PCT/US06/07757, Mailed on Jun. 27, 2006, 3 pages.
PCT/US06/62385 International Search Report and Written Opinion of the International Searching Authority, mailed Mar. 28, 2008, 16 pages.
Supplementary European Search Report for Application No. EP02756362, mailed on Jun. 9, 2008, 3 pages.
Supplementary Partial European Search Report for Application No. EP02748026, dated Jan. 14, 2011, 5 pages total.
Written Opinion for Application No. PCT/US06/07757, mailed on Jun. 27, 2006, 5 pages (ISRG00111US/PCT).

\* cited by examiner

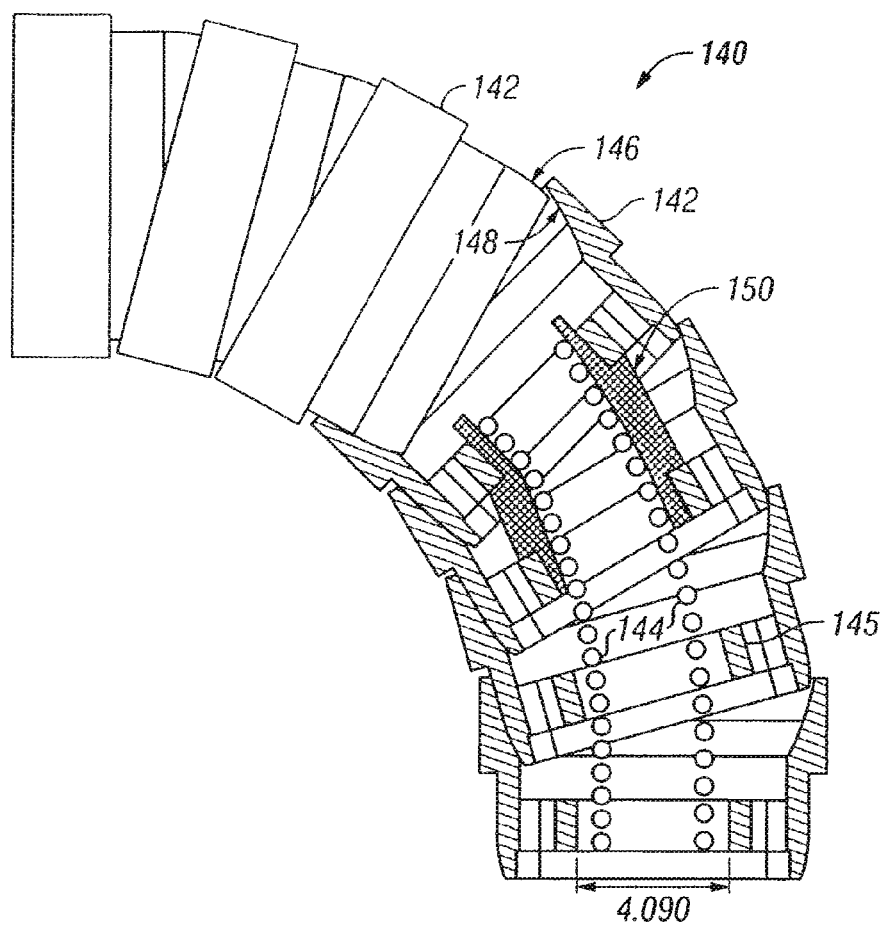
FIG. 15
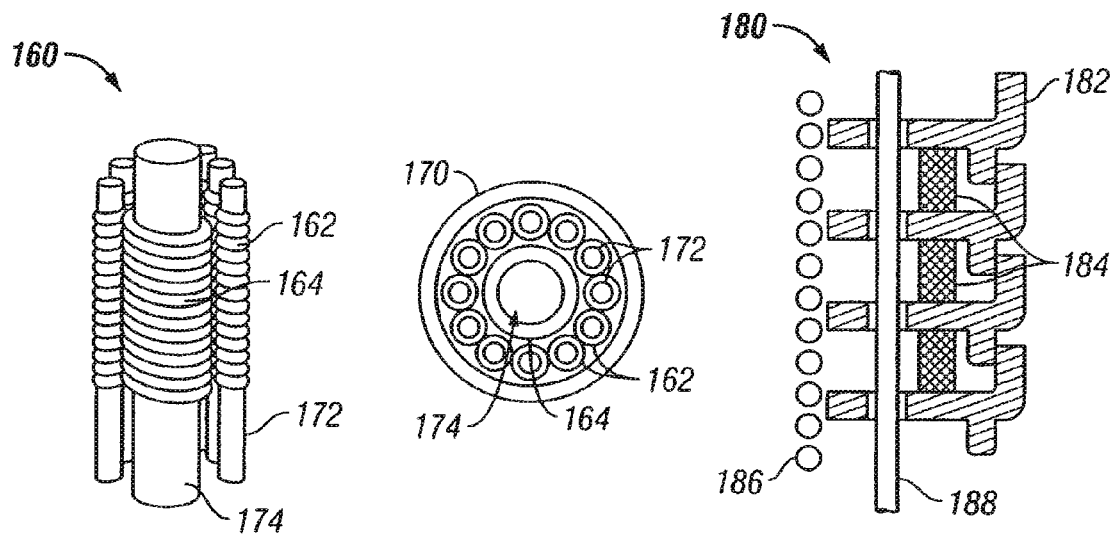
FIG. 16  FIG. 17  FIG. 18

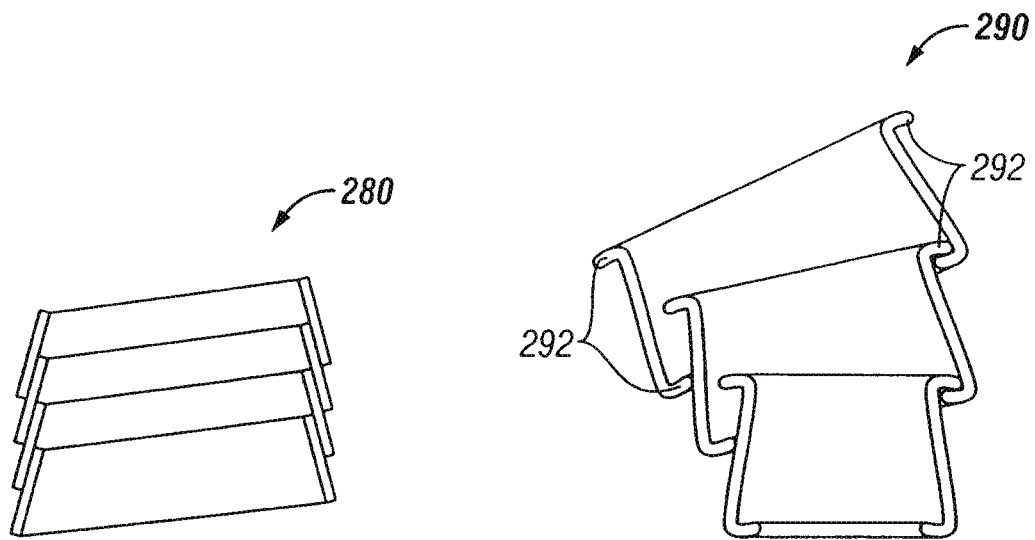
FIG. 28  FIG. 29
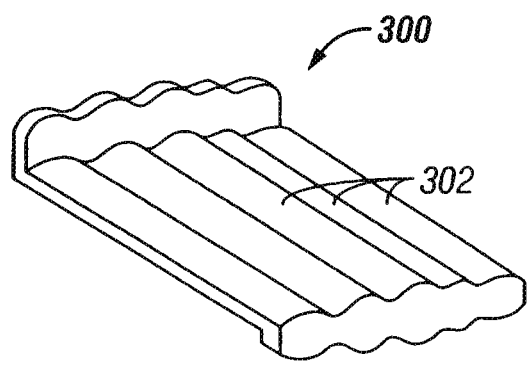
FIG. 30

FLEXIBLE WRIST FOR SURGICAL TOOL

CROSS-REFERENCES TO RELATED APPLICATIONS

This application is a division of prior application Ser. No. 12/948,641 entitled FLEXIBLE WRIST FOR SURGICAL TOOL by Cooper et al., filed Nov. 17, 2010, which is a continuation of prior application Ser. No. 11/733,879 entitled FLEXIBLE WRIST FOR SURGICAL TOOL by Cooper et al., filed Apr. 11, 2007, now U.S. Pat. No. 7,862,580, which is a continuation of prior application Ser. No. 10/726,795 entitled FLEXIBLE WRIST FOR SURGICAL TOOL by Cooper, et al., filed Dec. 2, 2003, now U.S. Pat. No. 7,320,700, which claims benefit of Provisional Application No. 60/431,636, filed Dec. 6, 2002. This application claims the benefit of these prior applications, which are incorporated herein by reference. This application is related to the following patents and patent applications, the full disclosure of which is incorporated herein by reference.

U.S. patent application Ser. No. 10/187,248, entitled "Surgical Tool Having Positively Positionable Tendon-Actuated Multi-Disk Wrist Joint," filed on Jun. 28, 2002;

U.S. patent application Ser. No. 10/186,176, entitled "Platform Link Wrist Mechanism", filed on Jun. 28, 2002;

PCT International Application No. PCT/US98/19508, entitled "Robotic Apparatus", filed on Sep. 18, 1998, and published as WO99/50721;

U.S. patent application Ser. No. 09/418,726, entitled "Surgical Robotic Tools, Data Architecture, and Use", filed on Oct. 15, 1999;

U.S. Patent Application No. 60/111,711, entitled "Image Shifting for a Telerobotic System", filed on Dec. 8, 1998;

U.S. patent application Ser. No. 09/378,173, entitled "Stereo Imaging System for Use in Telerobotic System", filed on Aug. 20, 1999;

U.S. patent application Ser. No. 09/398,507, entitled "Master Having Redundant Degrees of Freedom", filed on Sep. 17, 1999;

U.S. application Ser. No. 09/399,457, entitled "Cooperative Minimally Invasive Telesurgery System", filed on Sep. 17, 1999;

U.S. patent application Ser. No. 09/373,678, entitled "Camera Referenced Control in a Minimally Invasive Surgical Apparatus", filed on Aug. 13, 1999;

U.S. patent application Ser. No. 09/398,958, entitled "Surgical Tools for Use in Minimally Invasive Telesurgical Applications", filed on Sep. 17, 1999; and U.S. Pat. No. 5,808,665, entitled "Endoscopic Surgical Instrument and Method for Use", issued on Sep. 15, 1998.

BACKGROUND OF THE INVENTION

The present invention relates generally to surgical tools and, more particularly, to flexible wrist mechanisms in surgical tools for performing robotic surgery.

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

Some surgical tools employ a roll-pitch-yaw mechanism for providing three degrees of rotational movement to an end effector around three perpendicular axes. The pitch and yaw rotations are typically provided by a wrist mechanism coupled between a shaft of the tool and an end effector, and the roll rotation is typically provided by rotation of the shaft. At about 90° pitch, the yaw and roll rotational movements overlap, resulting in the loss of one degree of rotational movement, referred to as a singularity.

BRIEF SUMMARY OF THE INVENTION

The present invention is directed to alternative embodiments of a tool having a wrist mechanism that provides pitch and yaw rotation in such a way that the tool has no singularity in roll, pitch, and yaw. The wrist mechanism has a flexible tubular structure which may be formed by a flexible tube or a series of disks connected to a spring or similar flexible component. Actuation cables or flexible wires (e.g., made of nitinol) extend through the wrist mechanism, and are used to bend the flexible wrist in pitch and yaw rotation. The rotation in roll is provided by turning a tool shaft to which the wrist mechanism is attached.

In accordance with an aspect of the present invention, a wrist mechanism includes a minimally invasive surgical instrument comprises an elongate shaft having a working end, a proximal end, and a shaft axis between the working end and the proximal end; and an end effector. A wrist member has a flexible tube and an inner spring which include proximal portions connected to the working end of the elongate shaft and distal portions connected to the end effector. The inner spring is disposed inside an interior cavity of the flexible tube, and has an axis which is parallel to an axis of the flexible tube. A plurality of actuation cables (or wires) have distal portions connected to the end effector and extend from the distal portion through the wrist member toward the elongate shaft to proximal portions which are actuatable to bend the wrist member in pitch rotation and yaw rotation. If actuation wires are used they may also help support the end effector.

In some embodiments, the actuation cables are disposed inside a hollow interior of the inner spring. At least three actuation cables are connected to the end effector. The proximal portions of the actuation cables are connected to a gimbal plate configured to actuate the actuation cables, and the gimbal plate is disposed proximal of the proximal end of the elongate shaft. The actuation cables may be disposed between the inner spring and the flexible tube. The flexible tube may include interior axial slots bounded by an external surface of the inner spring to form lumens for receiving the actuation cables. The flexible tube may include a plurality of transverse cut-outs which are generally transverse to the axis of the flexible tube.

In accordance with another aspect of the invention, a minimally invasive surgical instrument comprises an elongate shaft having a working end, a proximal end, and a shaft axis between the working end and the proximal end; and an end effector. A wrist member has a flexible tube including an axis extending through an interior surrounded by a wall. The wall of the flexible tube includes a plurality of lumens oriented generally parallel to the axis of the flexible tube. The wrist member has a proximal portion connected to the working end of the elongate shaft and a distal portion connected to the end effector. A plurality of actuation cables have distal portions connected to the end effector and extend from the distal portion through the lumens of the wall of the wrist member toward the elongate shaft to proximal portions which are actuatable to bend the wrist member in pitch rotation and yaw rotation.

In some embodiments, the wall of the flexible tube includes twelve lumens. Each actuation cable is looped around a distal portion of the wall of the flexible tube to extend through two adjacent lumens. The flexible tube includes a plurality of transverse cut-outs which are generally transverse to the axis of the flexible tube. An outer cover is wrapped around an external surface of the flexible tube. The transverse cut-outs comprise alternating layers of cut-outs each having a pair of cut-outs which are disposed opposite to one another. The cut-outs of each layer are oriented in a direction which is spaced by about 90 degrees from the cut-outs of an adjacent layer. The transverse cut-outs leave ribs connected between disk portions above and below the ribs. Slits extending generally along the axis of the flexible tube into the disk portions may be provided on both sides of the ribs.

In specific embodiments, the flexible tube comprises an inner tube having a plurality of slots oriented generally parallel to the axis of the flexible tube and an outer cover wrapped around the inner tube to form the lumens at the slots. The outer cover comprises an exterior spring. The flexible tube may comprise a plurality of springs each disposed around one of the plurality of slots. An inner spring may be disposed around the interior of the flexible tube. A braided cover may be formed on an exterior surface of the flexible tube. The braided cover has a first set of wires wound in a clockwise direction between a proximal end and a distal end of the flexible tube and a second set of wires wound in a counterclockwise direction between the proximal end and the distal end of the flexible tube and interwoven with the first set of wires.

In some embodiments, the flexible tube comprises a plurality of axial sliding members which are slidably connected with each other by an axial connection generally parallel to the axis of the flexible tube. The axial connection comprises a tongue and groove connection. Each axial sliding member includes a lumen for receiving one of the actuation cables in another version. The flexible tube comprises a plurality of axial springs coupled with each other and disposed around a circumference of the flexible tube. Each axial spring has coils which overlap with coils of an adjacent axial spring to provide one of the lumens for receiving one of the actuation cables. The flexible tube may comprise a wave spring having a plurality of wave spring segments which include high points and low points connected in series along the axis of the flexible tube. The high points of one wave spring segment are connected to the low points of an adjacent wave spring segment.

In accordance with another aspect of the present invention, a minimally invasive surgical instrument comprises an elongate shaft having a working end, a proximal end, and a shaft axis between the working end and the proximal end; and an end effector. A wrist member has an inner spring which includes a proximal portion connected to the working end of the elongate shaft and a distal portion connected to the end effector. The wrist member has a plurality of annular disks distributed along an axis of the inner spring. The annular disks each have an inside edge connected with the inner spring. A plurality of actuation cables have distal portions connected to the end effector and extend from the distal portion through the wrist member toward the elongate shaft to proximal portions which are actuatable to bend the wrist member in pitch rotation and yaw rotation.

In some embodiments, the disks include a plurality of holes through which the actuation cables extend. The disks each include a pair of inner tabs disposed opposite from one another and extending from the inside edge into a gap between coils of the inner spring. Adjacent disks are oriented with the inner tabs of one disk disposed about 90 degrees apart from the inner tabs of the adjacent disk. The disks each include an outer mating surface and an inner mating surface for mating between adjacent disks, the outer mating surface of one disk mating with the inner mating surface of the adjacent disk. The outer mating surface and the inner mating surface are generally spherical in shape. A plurality of elastomer members each disposed between and connected with adjacent disks. A wrist cover is disposed outside of the inner spring and the annular disks. The wrist cover comprises a flat spiral of non-conductive material. The flat spiral includes curled edges which overlap between adjacent layers of the spiral. The flat spiral includes grooves oriented generally parallel to the axis of the inner spring.

BRIEF DESCRIPTION OF THE DRAWINGS

FIG. 15 is a partial sectional view of the wrist of FIG. 14 in bending;

FIG. 16 is a perspective view of a wrist according to another embodiment of the invention;

FIG. 17 is a plan view of the wrist of FIG. 16;

FIG. 18 is a cross-sectional view of a portion of a wrist according to another embodiment of the invention;

FIG. 28 is an cross-sectional view of a wrist cover according to an embodiment of the invention;

FIG. 29 is an cross-sectional view of a wrist cover according to another embodiment of the invention; and FIG. 30 is a perspective view of a portion of a wrist cover according to another embodiment of the invention.

DETAILED DESCRIPTION OF THE INVENTION

As used herein, "end effector" refers to an actual working distal part that is manipulable by means of the wrist member for a medical function, e.g., for effecting a predetermined treatment of a target tissue. For instance, some end effectors have a single working member such as a scalpel, a blade, or an electrode. Other end effectors have a pair or plurality of working members such as forceps, graspers, scissors, or clip appliers, for example. In certain embodiments, the disks or vertebrae are configured to have openings which collectively define a longitudinal lumen or space along the wrist, providing a conduit for any one of a number of alternative elements or instrumentalities associated with the operation of an end effector. Examples include conductors for electrically activated end effectors (e.g., electrosurgical electrodes; transducers, sensors, and the like); conduits for fluids, gases or solids (e.g., for suction, insufflation, irrigation, treatment fluids, accessory introduction, biopsy extraction and the like); mechanical elements for actuating moving end effector members (e.g., cables, flexible elements or articulated elements for operating grips, forceps, scissors); wave guides; sonic conduction elements; fiberoptic elements; and the like. Such a longitudinal conduit may be provided with a liner, insulator or guide element such as a elastic polymer tube; spiral wire wound tube or the like.

As used herein, the terms "surgical instrument", "instrument", "surgical tool", or "tool" refer to a member having a working end which carries one or more end effectors to be introduced into a surgical site in a cavity of a patient, and is actuatable from outside the cavity to manipulate the end effector(s) for effecting a desired treatment or medical function of a target tissue in the surgical site. The instrument or tool typically includes a shaft carrying the end effector(s) at a distal end, and is preferably servomechanically actuated by a telesurgical system for performing functions such as holding or driving a needle, grasping a blood vessel, and dissecting tissue.

The various embodiments of the flexible wrist described herein are intended to be relatively inexpensive to manufacture and be capable of use for cautery, although they are not limited to use for cautery. For MIS applications, the diameter of the insertable portion of the tool is small, typically about 12 mm or less, and preferably about 5 mm or less, so as to permit small incisions. It should be understood that while the examples described in detail illustrate this size range, the embodiments may be scaled to include larger or smaller instruments.

Figure 14:
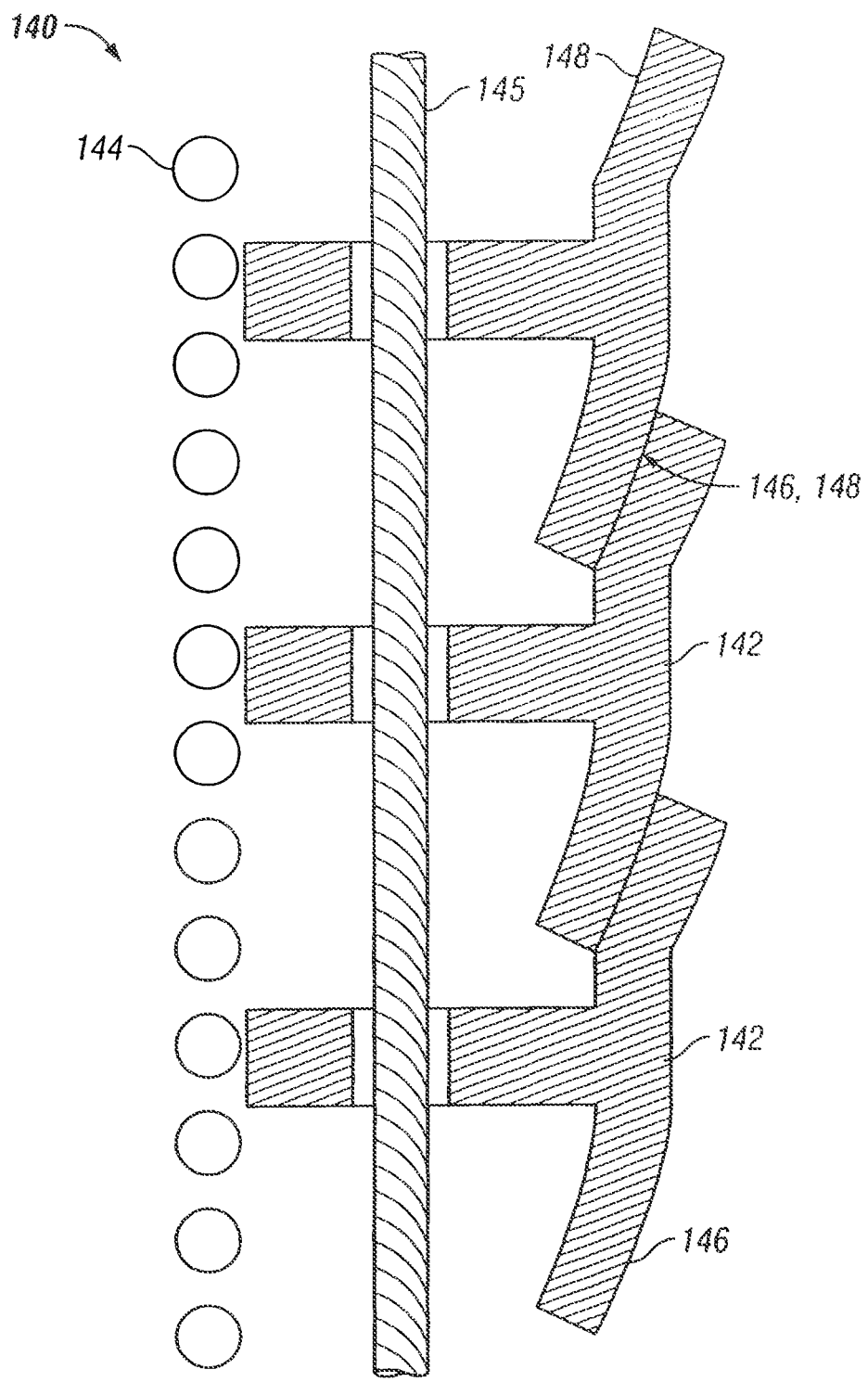
FIG. 14 is a cross-sectional view of a portion of a wrist according to another embodiment of the invention.
Figure 22:
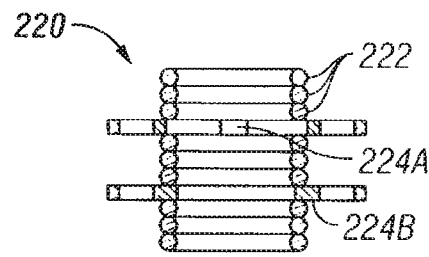
FIG. 22 is a cross-sectional view of a portion of a wrist according to another embodiment of the invention.

Some of the wrist embodiments employ a series of disks or similar elements that move in a snake-like manner when bent in pitch and yaw (e.g., FIGS. 14 and 22). The disks are annular disks and may have circular inner and outer diameters. Typically, those wrists each include a series of disks, for example, about thirteen disks, which may be about 0.005 inch to about 0.030 inch thick, etched stainless steel disks. Thinner disks may be used in the middle, while thicker disks are desirable for the end regions for additional strength to absorb cable forces such as those that are applied at the cable U-turns around the end disk. The end disk may include a counter bore (e.g., about 0.015 inch deep) into which the center spring fits to transfer the load from the cables into compression of the center spring. The disks may be threaded onto an inner spring, which acts as a lumen for pulling cables for an end effector such as a gripper, a cautery connection, or a tether to hold a tip thereon. The inner spring also provides axial stiffness, so that the gripper or tether forces do not distort the wrist. In some embodiments, the disks include a pair of oppositely disposed inner tabs or tongues which are captured by the inner spring. The inner spring is at solid height (the wires of successive helix pitches lie in contact with one another when the spring is undeflected), except at places where the tabs of the disks are inserted to create gaps in the spring. The disks alternate in direction of the tabs to allow for alternating pitch and yaw rotation. A typical inner spring is made with a 0.01 inch diameter wire, and adjacent disks are spaced from one another by four spring coils. If the spring is made of edge wound flat wire (like a slinky), high axial force can be applied by the cables without causing neighboring coils to hop over each other.

In some embodiments, each disk has twelve evenly spaced holes for receiving actuation cables. Three cables are sufficient to bend the wrist in any desired direction, the tensions on the individual cables being coordinated to produce the desired bending motion. Due to the small wrist diameter and the moments exerted on the wrist by surgical forces, the stress in the three cables will be quite large. More than three cables are typically used to reduce the stress in each cable (including additional cables which are redundant for purposes of control). In some examples illustrated below, twelve or more cables are used (see discussion of FIG. 4 below). To drive the cables, a gimbal plate or rocking plate may be used. The gimbal plate utilizes two standard inputs to manipulate the cables to bend the wrist at arbitrary angles relative to the pitch and yaw axes.

Figure 2:
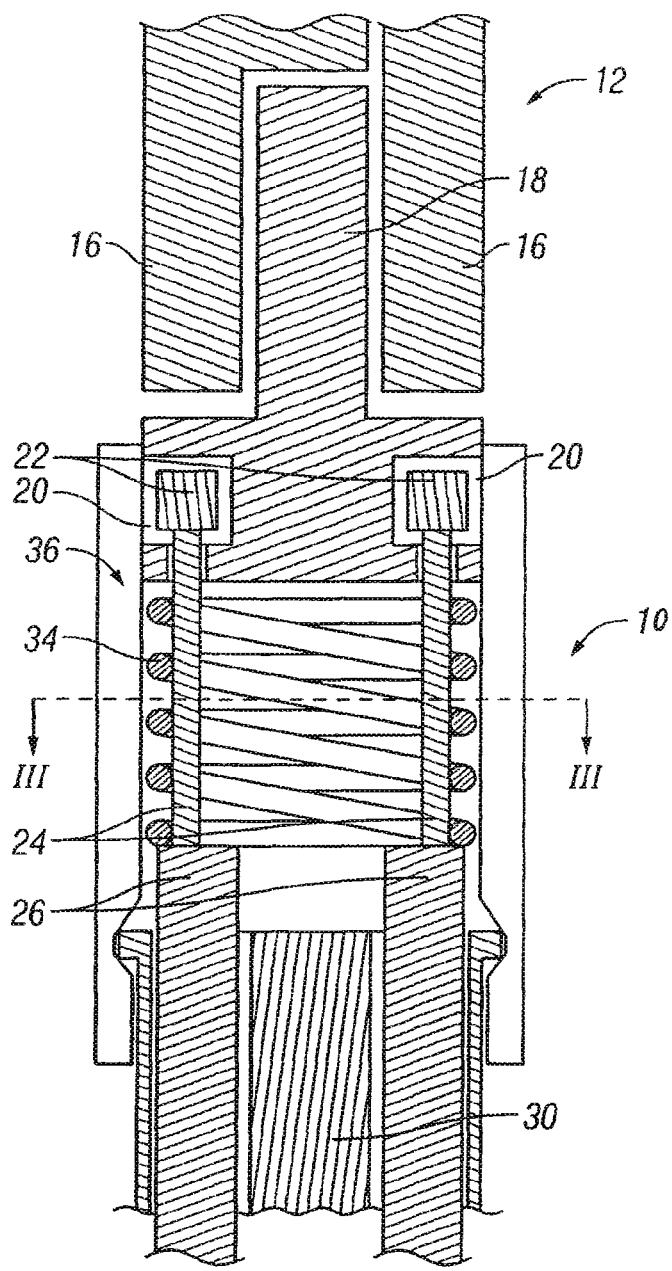
FIG. 2 is a cross-sectional view of a wrist according to an embodiment of the present invention.
Figure 4:
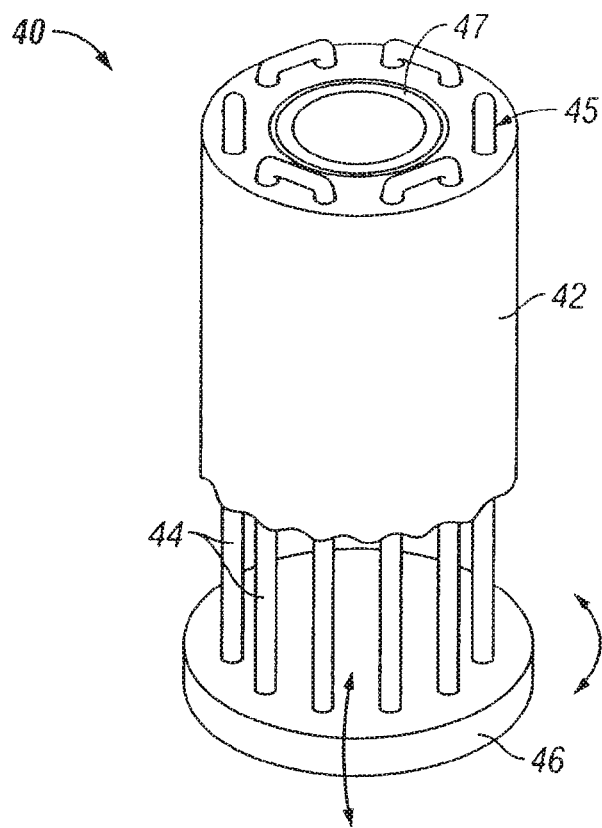
FIG. 4 is a perspective view of a wrist according to another embodiment of the invention.

Some wrists are formed from a tubular member that is sufficiently flexible to bend in pitch and yaw (e.g., FIGS. 2 and 4). An inner spring may be included. The tubular member may include cut-outs to reduce the structural stiffness to facilitate bending (e.g., FIGS. 5 and 19). One way to make the wrist is to insert wire and hypotube mandrels in the center hole and the actuation wire holes. A mold can be made, and the assembly can be overmolded with a two-part platinum cure silicone rubber cured in the oven (e.g., at about 165° C.). The mandrels are pulled out after molding to create channels to form the center lumen and peripheral lumens for the pulling cables. In this way, the wrist has no exposed metal parts. The rubber can withstand autoclave and can withstand the elongation during wrist bending, which is typically about 30% strain.

Figure 8:
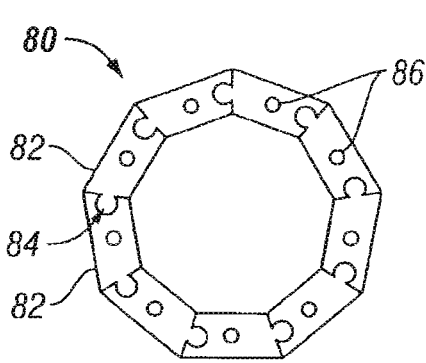
FIG. 8 is a plan view of a wrist according to another embodiment of the invention.

In specific embodiments, the tubular member includes a plurality of axial sliding members each having a lumen for receiving an actuation cable (e.g., FIG. 8). The tubular member may be formed by a plurality of axial springs having coils which overlap with the coils of adjacent springs to provide lumens for receiving the actuation cables (e.g., FIG. 10). The tubular member may be formed by a stack of wave springs (e.g., FIG. 12). The lumens in the tubular member may be formed by interiors of axial springs (e.g., FIG. 16). The exterior of the tubular member may be braided to provide torsional stiffness (e.g., FIG. 27).

A. Wrist Having Wires Supported by Wire Wrap

Figure 1:
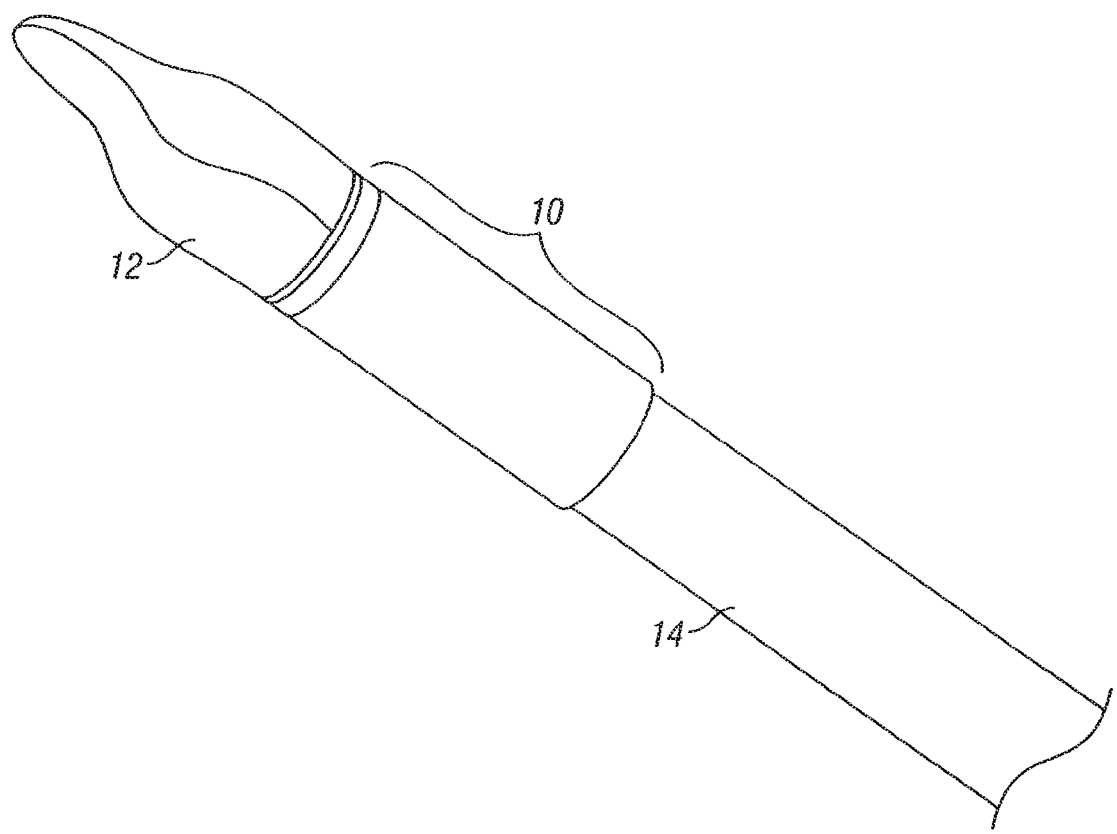
FIG. 1 is a perspective of a surgical tool according to an embodiment of the invention.

FIG. 1 shows a wrist 10 connected between a distal end effector 12 and a proximal tool shaft or main tube 14 for a surgical tool. The end effector 12 shown includes grips 16 mounted on a distal clevis 18, as best seen in FIG. 2. The distal clevis 18 includes side access slots 20 that house distal crimps 22 of a plurality of wires or cables 24 that connect proximally to hypotubes 26, which extend through a platform or guide 30 and the interior of the tool shaft 14. The guide 30 orients the hypotubes 26 and wire assembly, and is attached the tool shaft 14 of the instrument. The guide 30 also initiates the rolling motion of the wrist 10 as the tool shaft 14 is moved in roll. The side access slots 20 conveniently allow the crimps 22 to be pressed into place. Of course, other ways of attaching the wires 24 to the distal clevis 18, such as laser welding, may be employed in other embodiments.

Figure 3:
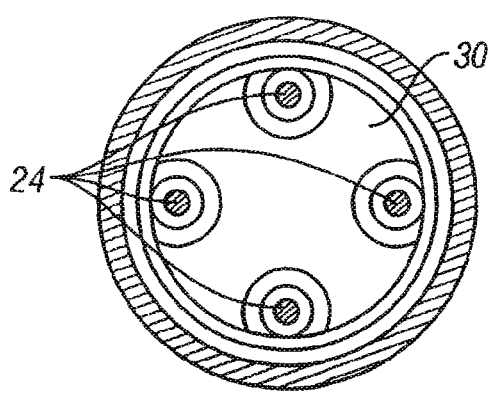
FIG. 3 is cross-sectional view of the wrist of FIG. 2 along III-III.
Figure 27:
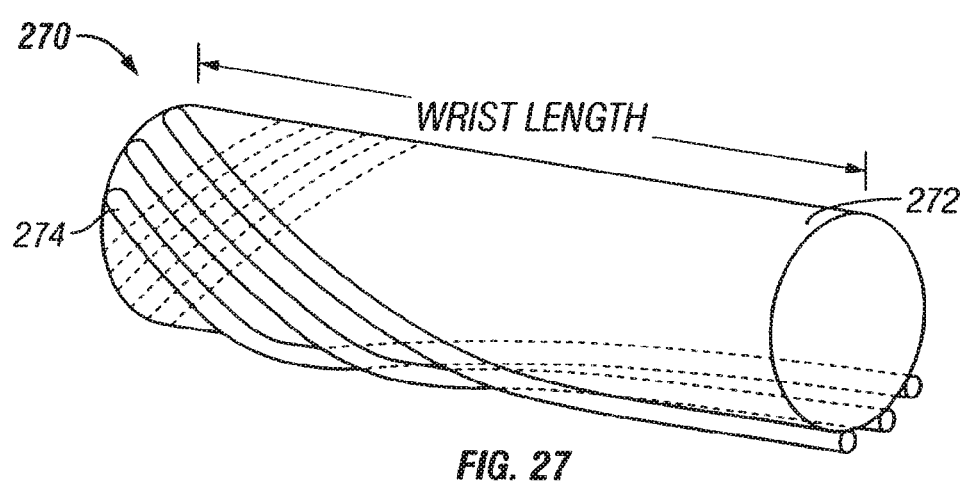
FIG. 27 is a perspective view of a wrist according to another embodiment of the invention.

FIGS. 2 and 3 show four wires 24, but a different number of wires may be used in another embodiment. The wires 24 may be made of nitinol or other suitable materials. The wires 24 create the joint of the wrist 10, and are rigidly attached between the distal clevis 18 and the hypotubes 26. A wire wrap 34 is wrapped around the wires 24 similar to a coil spring and extends between the distal clevis 18 and the hypotubes 26. The shrink tube 36 covers the wire wrap 34 and portions of the distal clevis 18 and the guide 30. The wire wrap 34 and shrink tube 36 keep the wires 24 at fixed distances from each other when the hypotubes 26 are pushed and pulled to cause the wrist 10 to move in pitch and yaw. They also provide torsional and general stiffness to the wrist 10 to allow it to move in roll with the tool shaft 14 and to resist external forces. The wire wrap and shrink tube can be configured in different ways in other embodiments (one preferred embodiment is shown in FIG. 27 and described in Section J below). For example, they can be converted into a five-lumen extrusion with the wires 24 as an internal part. The function of the wire wrap or an equivalent structure is to keep the wires 24 at a constant distance from the center line as the wrist 10 moves in roll, pitch, and/or yaw. The shrink tube can also provide electrical isolation.

B. Wrist Having Flexible Tube Bent by Actuation Cables

FIG. 4 shows a wrist 40 that includes a tube 42 having holes or lumens 43 distributed around the circumference to receive actuation cables or wires 44, which may be made of nitinol. The tube 42 is flexible to permit bending in pitch and yaw by pulling the cables 44. The wrist 40 preferably includes a rigid distal termination disk 41 (as shown in an alternative embodiment of FIG. 4B) or other reinforcement that is substantially more rigid than the flexible tube 42 to evenly distribute cable forces to the flexible tube 42. The hollow center of the tube 42 provides room for end effector cables such as gripping cables. There are typically at least four lumens. An inner spring 47 may be provided.

FIG. 4 shows twelve lumens for the specific embodiment to accommodate six cables 44 making U-turns 45 at the distal end of the tube 42. The high number of cables used allows the tube 42 to have a higher stiffness for the same cable pulling force to achieve the same bending in pitch and yaw. For example, the use of twelve cables instead of four cables means the tube 42 can be three times as stiff for the same cable pulling force. Alternatively, if the stiffness of the tube 42 remains the same, the use of twelve cables instead of four cables will reduce the cable pulling force required by a factor of three. Note that although the material properties and cable stress levels may permit the U-turns 45 to bear directly on the end of the tube 42, a reinforced distal termination plate 41 may be included to distribute cable forces more smoothly over the tube 42. The proximal ends of the cables 44 may be connected to an actuator mechanism, such as an assembly including a gimbal plate 46 that is disclosed in U.S. patent application Ser. No. 10/187,248, filed on Jun. 27, 2002, the full disclosure of which is incorporated herein by reference. This mechanism facilitates the actuation of a selected plurality of cables in a coordinated manner for control of a bendable or steerable member, such as controlling the flexible wrist bending angle and direction. The example of an actuator mechanism of application Ser. No. 10/187,248 can be adapted to actuate a large number of peripheral cables in a proportionate manner so as to provide a coordinated steering of a flexible member without requiring a comparably large number of linear actuators. Alternatively, a separately controlled linear actuation mechanism may be used to tension each cable or cable pairs looped over a pulley and moved with a rotary actuator, the steering being controlled by coordinating the linear actuators.

The tube 42 typically may be made of a plastic material or an elastomer with a sufficiently low modulus of elasticity to permit adequate bending in pitch and yaw, and may be manufactured by a multi-lumen extrusion to include the plurality of lumens, e.g., twelve lumens. It is desirable for the tube to have a high bending stiffness to limit undesirable deflections such as S-shape bending, but this increases the cable forces needed for desirable bending in pitch and yaw. As discussed below, one can use a larger number of cables than necessary to manipulate the wrist in pitch and yaw (i.e., more than three cables) in order to provide sufficiently high cable forces to overcome the high bending stiffness of the tube.

Figure 4A:
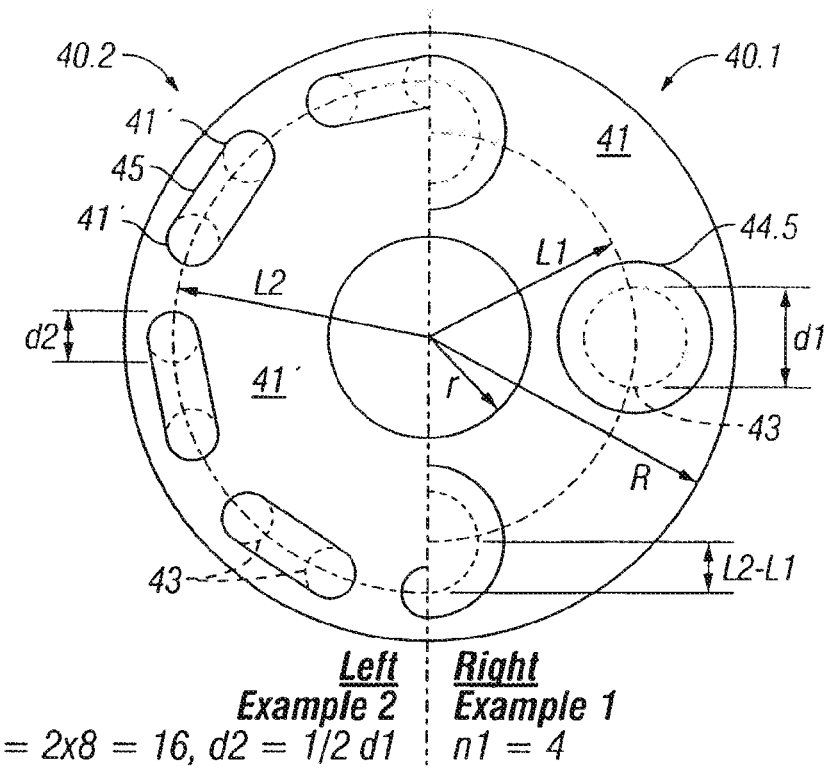
FIGS. 4A and 4B are, respectively, a plan view and an elevation view of a distal portion of an example of a wrist similar to that of FIG. 4, showing details of the cable arrangement.
Figure 4B:
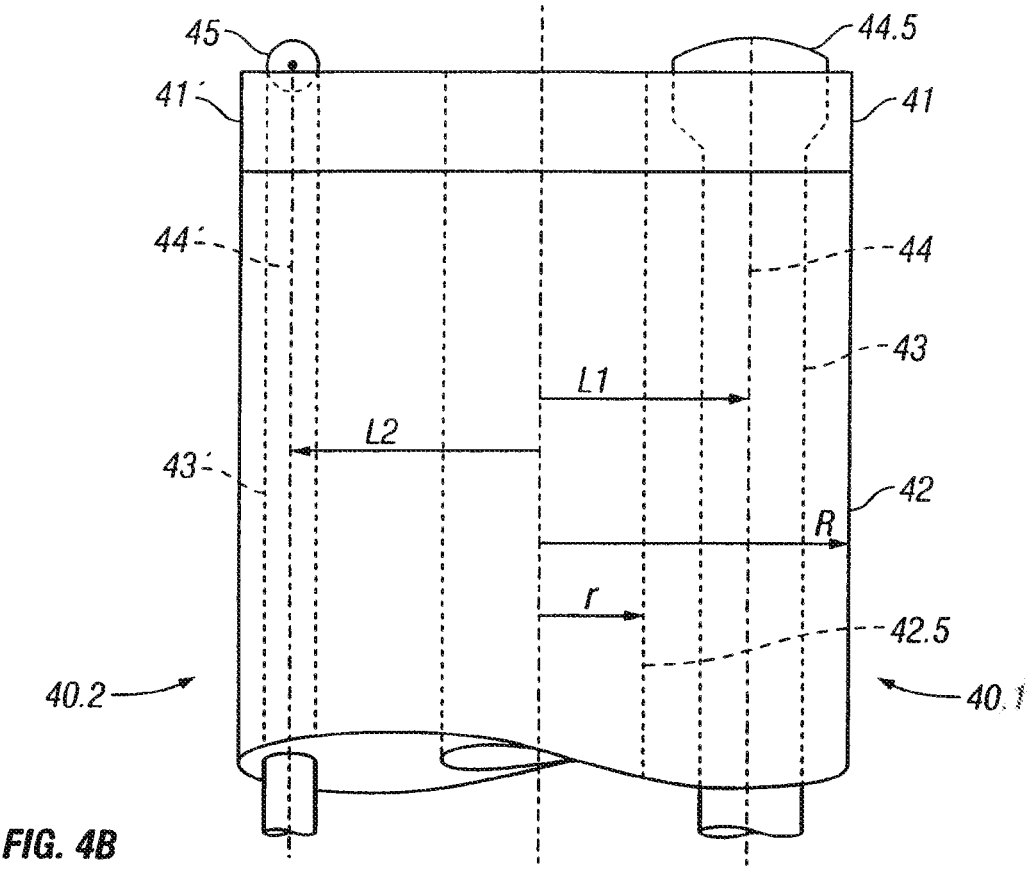

FIGS. 4A and 4B show schematically an example of two different cable arrangements in a wrist embodiment similar to that shown in FIG. 4. Note that for constant total cable cross-sectional area, including cables in pairs and including a greater number of proportionately smaller cables both permit the cables to terminate at a greater lateral offset relative to the wrist centerline. FIGS. 4A and 4B show a plan view and an elevational view respectively of a wrist embodiment, split by a dividing line such that the right side of each figure shows a wrist Example 1, and the left side of each figure shows a wrist Example 2. In each example the tube 42 has the same outside radius R and inside radius r defining the central lumen.

In Example 1, the number of cables 44 in the wrist 40.1 is equal to four (n1=4) with each cable individually terminated by a distal anchor 44.5, set in a countersunk bore in the distal termination plate 41, each cable extending through a respective lateral cable lumen 43 in the distal termination plate 41 and the flexible tube 42. The anchor 44.5 may be a swaged bead or other conventional cable anchor.

In Example 2, the number of cables 44' in the wrist 40.2 is equal to sixteen (n2=16), with the cables arranged as eight symmetrically spaced pairs of portions 44', each pair terminated by a distal "U-turn" end loop 45 bearing on the distal termination plate 41' between adjacent cable lumens 43'. The edges of the distal termination plate 41' at the opening of lumens 43' may be rounded to reduce stress concentration, and the loop 45 may be partially or entirely countersunk into the distal termination plate 41. The diameters of the sixteen cables 44' are ½ the diameters of the four cables 44, so that the total cross-sectional cable area is the same in each example.

Comparing Examples 1 and 2, the employment of termination loop 45 eliminates the distal volume devoted to a cable anchor 44.5, and tends to permit the cable lumen 43' to be closer to the radius R of the tube 42 than the cable lumen 43. In addition, the smaller diameter of each cable 44' brings the cable centerline closer to the outer edge of the cable lumen 43'. Both of these properties permit the cables in Example 2 to act about a larger moment arm L2 relative to the center of tube 42 than the corresponding moment arm L1 of Example 1. This greater moment arm L2 permits lower cable stresses for the same overall bending moment on the tube 42 (permitting longer cable life or a broader range of optional cable materials), or alternatively, a larger bending moment for the same cable stresses (permitting greater wrist positioning stiffness). In addition, smaller diameter cables may be more flexible than comparatively thicker cables. Thus a preferred embodiment of the wrist 40 includes more that three cables, preferably at least 6 (e.g., three pairs of looped cables) and more preferably twelve or more.

Note that the anchor or termination point shown at the distal termination plate 41 is exemplary, and the cables may be terminated (by anchor or loop) to bear directly on the material of the tube 42 if the selected material properties are suitable for the applied stresses. Alternatively, the cables may extend distally beyond the tube 42 and/or the distal termination plate 41 to terminate by connection to a more distal end effector member (not shown), the cable tension being sufficiently biased to maintain the end effector member securely connected to the wrist 40 within the operational range of wrist motion.

Figure 5:
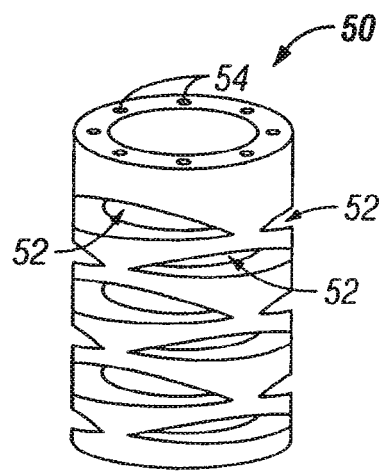
FIG. 5 is a perspective view of a wrist according to another embodiment of the invention.

One way to reduce the stiffness of the tube structurally is to provide cutouts, as shown in FIG. 5. The tube 50 includes a plurality of cutouts 52 on two sides and alternating in two orthogonal directions to facilitate bending in pitch and yaw, respectively. A plurality of lumens 54 are distributed around the circumference to accommodate actuation cables.

Figure 6:
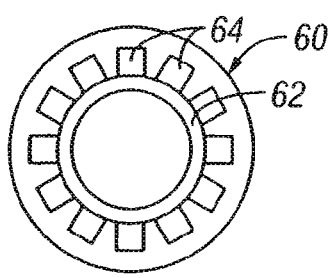
FIG. 6 is a plan view of a wrist according to another embodiment of the invention.

In another embodiment illustrated in FIG. 6, the tube 60 is formed as an outer boot wrapped around an interior spring 62 which is formed of a higher stiffness material than that for the tube 60. The tube 60 includes interior slots 64 to receive actuation cables. Providing a separately formed flexible tube can simplify assembly. Such a tube is easier to extrude, or otherwise form, than a tube with holes for passing through cables. The tube also lends itself to using actuation cables with preformed termination structures or anchors, since the cables can be put in place from the central lumen, and then the inner spring inserted inside the cables to maintain spacing and retention of the cables. In some cases, the tube 60 may be a single use component that is sterile but not necessarily autoclavable.

Figure 7:
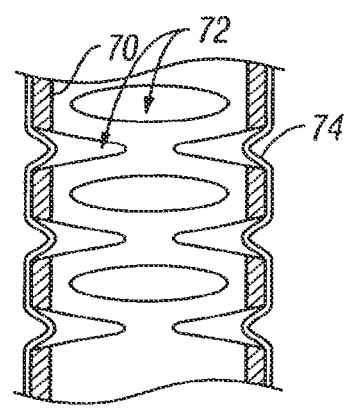
FIG. 7 is a cross-sectional view of a wrist according to another embodiment of the invention.

FIG. 7 shows a tube 70 having cutouts 72 which may be similar to the cutouts 52 in the tube 50 of FIG. 5. The tube 70 may be made of plastic or metal. An outer cover 74 is placed around the tube 50. The outer cover 74 may be a Kapton cover or the like, and is typically a high modulus material with wrinkles that fit into the cutouts 72.

C. Wrist Having Axial Tongue and Groove Sliding Members

Figure 9:
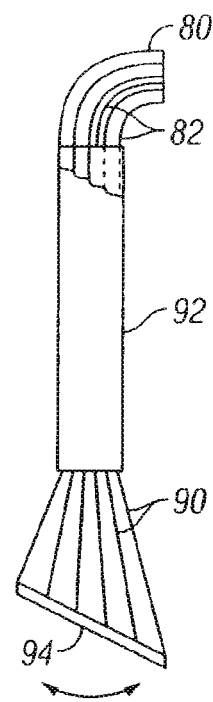
FIG. 9 is an elevational view of the wrist of FIG. 8 with a tool shaft and a gimbal plate.

FIGS. 8 and 9 show a wrist 80 having a plurality of flexible, axially sliding members 82 that are connected or interlocked to each other by an axial tongue and groove connection 84 to form a tubular wrist 80. Each sliding member 82 forms a longitudinal segment of the tube 80. The axial connection 84 allows the sliding members 82 to slide axially relative to each other, while maintaining the lateral position of each member relative to the wrist longitudinal centerline. Each sliding member 82 includes a hole or lumen 86 for receiving an actuation cable, which is terminated adjacent the distal end of the wrist 80. FIG. 9 illustrates bending of the wrist 80 under cable pulling forces of the cables 90 as facilitated by sliding motion of the sliding members 82. The cables 90 extend through the tool shaft 92 and are connected proximally to an actuation mechanism, such as a gimbal plate 94 for actuation. The sliding members 82 bend by different amounts due to the difference in the radii of curvature for the sliding members 82 during bending of the wrist 80. Alternatively, an embodiment of a wrist having axially sliding members may have integrated cables and sliding members, for example whereby the sliding members are integrally formed around the cables (e.g., by extrusion) as integrated sliding elements, or whereby an actuation mechanism couples to the proximal ends of the sliding members, the sliding members transmitting forces directly to the distal end of the wrist.

Figure 13:
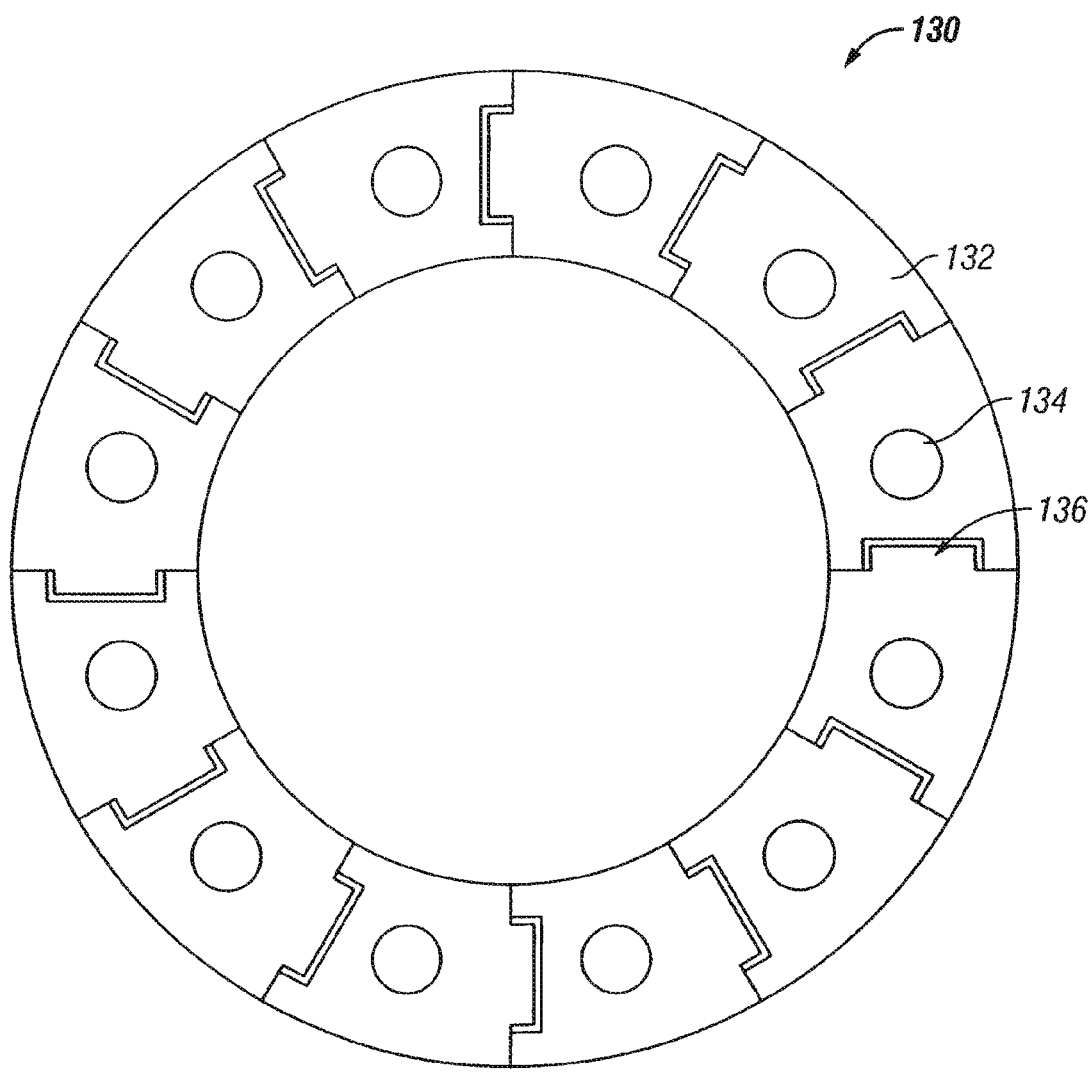
FIG. 13 is a plan view of a wrist according to another embodiment of the invention.

FIG. 13 shows a wrist 130 having a plurality of axial members 132 that are typically made of a flexible plastic material. The axial members 132 may be co-extruded over the cables 134, so that the cables can be metal and still be isolated. The axial members 132 may be connected to each other by an axial tongue and groove connection 136 to form a tubular wrist 130. The axial members 132 may be allowed to slide relative to each other during bending of the wrist 130 in pitch and yaw. The wrist 130 is similar to the wrist 80 of FIG. 8 but has a slightly different configuration and the components have different shapes.

D. Wrist Having Overlapping Axial Spring Members

Figure 11:
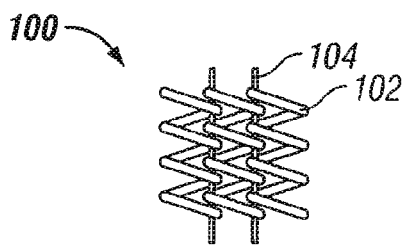
FIG. 11 is an elevational view of the wrist of FIG. 10.
Figure 10:
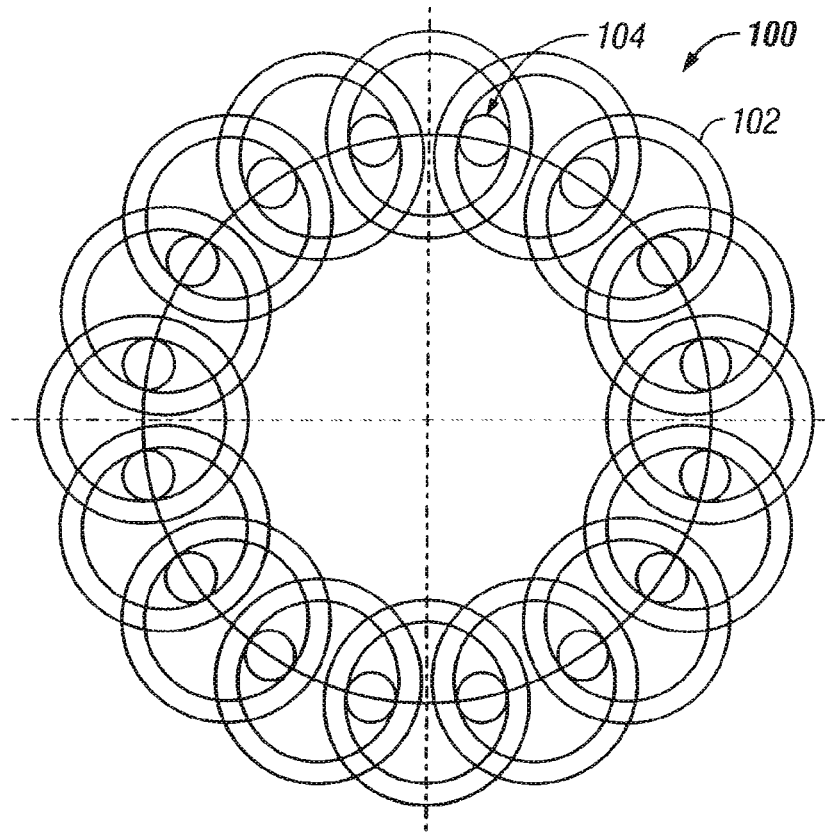
FIG. 10 is a plan view of a wrist according to another embodiment of the invention.

FIGS. 10 and 11 show a wrist 100 formed by a plurality of axial springs 102 arranged around a circumference to form a tubular wrist 100. The springs 102 are coil springs wound in the same direction or, more likely, in opposite directions. A cable 104 extends through the overlap region of each pair of adjacent springs 102, as more clearly seen in FIG. 11. Due to the overlap, the solid height of the wrist 100 would be twice the solid height of an individual spring 102, if the wrist is fully compressed under cable tension. The springs 102 are typically preloaded in compression so that the cables are not slack and to increase wrist stability.

In one alternative, the springs are biased to a fully compressed solid height state by cable pre-tension when the wrist is neutral or in an unbent state. A controlled, coordinated decrease in cable tension or cable release on one side of the wrist permits one side to expand so that the springs on one side of the wrist 100 expand to form the outside radius of the bent wrist 100. The wrist is returned to the straight configuration upon reapplication of the outside cable pulling force.

In another alternative, the springs are biased to a partially compressed state by cable pre-tension when the wrist is neutral or in an unbent state. A controlled, coordinated increase in cable tension or cable pulling on one side of the wrist permits that side to contract so that the springs on one side of wrist 100 shorten to form the inside radius of the bent wrist 100. Optionally this can be combined with a release of tension on the outside radius, as in the first alternative above. The wrist is returned to the straight configuration upon restoration of the original cable pulling force.

E. Wrist Having Wave Spring Members

Figure 12:
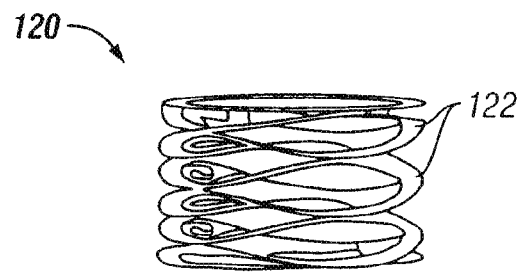
FIG. 12 is an elevational view of a wrist according to another embodiment of the invention.

FIG. 12 shows a wrist in the form of a wave spring 120 having a plurality of wave spring segments or components 122 which are stacked or wound to form a tubular, wave spring wrist 120. In one embodiment, the wave spring is formed and wound from a continuous piece of flat wire in a quasi-helical fashion, wherein the waveform is varied each cycle so that high points of one cycle contact the low points of the next. Such springs are commercially available, for instance, from the Smalley Spring Company. Holes are formed in the wave spring wrist 120 to receive actuation cables. Alternatively, a plurality of separate disk-like wave spring segments may be strung bead-fashion on the actuator cables (retained by the cables or bonded to one another).

The wave spring segments 122 as illustrated each have two opposite high points and two opposite low points which are spaced by 90 degrees. This configuration facilitates bending in pitch and yaw. Of course, the wave spring segments 122 may have other configurations such as a more dense wave pattern with additional high points and low points around the circumference of the wrist 120.

F. Wrist Having Disks with Spherical Mating Surfaces

FIG. 14 shows several segments or disks 142 of the wrist 140. An interior spring 144 is provided in the interior space of the disks 142, while a plurality of cables or wires 145 are used to bend the wrist 140 in pitch and yaw. The disks 142 are threaded or coupled onto the inner spring 144, which acts as a lumen for pulling cables for an end effector. The inner spring 144 provides axial stiffness, so that the forces applied through the pulling cables to the end effector do not distort the wrist 140. In alternative embodiments, stacked solid spacers can be used instead of the spring 144 to achieve this function. The disks 142 each include a curved outer mating surface 146 that mates with a curved inner mating surface 148 of the adjacent disk. FIG. 15 illustrates bending of the wrist 140 with associated relative rotation between the disks 142. The disks 142 may be made of plastic or ceramic, for example. The friction between the spherical mating surfaces 146, 148 preferably is not strong enough to interfere with the movement of the wrist 140. One way to alleviate this potential problem is to select an appropriate interior spring 144 that would bear some compressive loading and prevent excessive compressive loading on the disks 142 during actuation of the cables 145 to bend the wrist 140. The interior spring 144 may be made of silicone rubber or the like. An additional silicon member 150 may surround the actuation cables as well. In alternate embodiments, the separate disks 142 may be replaced by one continuous spiral strip.

In alternate embodiments, each cable in the wrist 160 may be housed in a spring wind 162 as illustrated in FIGS. 16 and 17. An interior spring 164 is also provided. The disks 170 can be made without the annular flange and holes to receive the cables (as in the disks 142 in FIGS. 14 and 15). The solid mandrel wires 172 inside of the spring winds 162 can be placed in position along the perimeters of the disks 170. A center wire mandrel 174 is provided in the middle for winding the interior spring 164. The assembly can be potted in silicone or the like, and then the mandrel wires 172, 174 can be removed. Some form of cover or the like can be used to prevent the silicone from sticking to the spherical mating surfaces of the disks 170. The small mandrel springs 172 will be wound to leave a small gap (instead of solid height) to provide room for shrinking as the wrist 160 bends. The silicone desirably is bonded sufficiently well to the disks 170 to provide torsional stiffness to the bonded assembly of the disks 170 and springs 172, 174. The insulative silicone material may serve as cautery insulation for a cautery tool that incorporates the wrist 160.

G. Wrist Having Disks Separated by Elastomer Members

FIG. 18 shows a wrist 180 having a plurality of disks 182 separated by elastomer members 184. The elastomer members 184 may be annular members, or may include a plurality of blocks distributed around the circumference of the disks 182. Similar to the wrist 140 of FIG. 14, an interior spring 186 is provided in the interior space of the disks 182 and the elastomer members 184, while a plurality of cables or wires 188 are used to bend the wrist 180 in pitch and yaw. The disks 182 are threaded or coupled onto the inner spring 184, which acts as a lumen for pulling cables for an end effector. The inner spring 184 provides axial stiffness, so that the forces applied through the pulling cables to the end effector do not distort the wrist 180. The configuration of this wrist 180 is more analogous to a human spine than the wrist 140. The elastomer members 184 resiliently deform to permit bending of the wrist 180 in pitch and yaw. The use of the elastomer members 184 eliminates the need for mating surfaces between the disks 182 and the associated frictional forces.

H. Wrist Having Alternating Ribs Supporting Disks for Pitch and Yaw Bending

Figure 19:
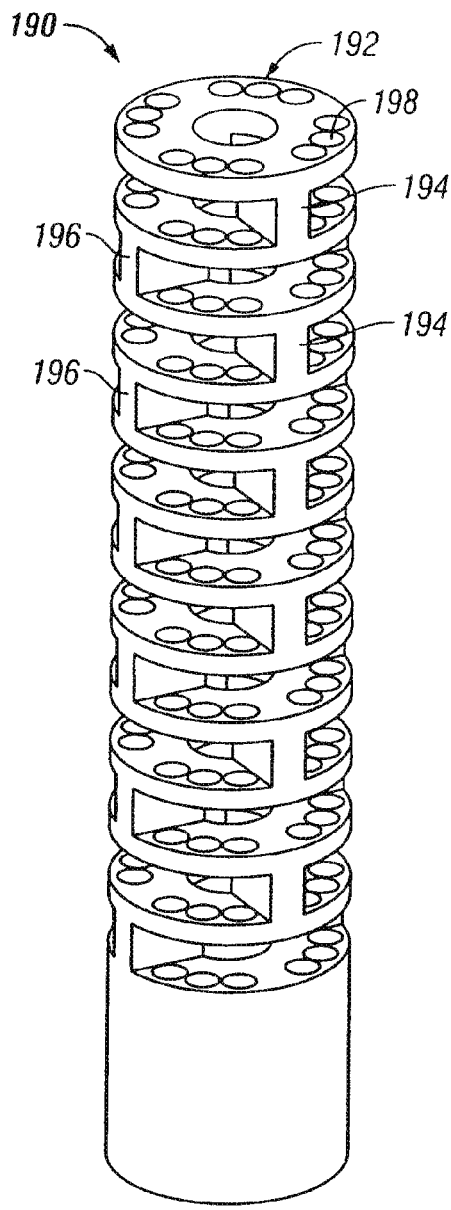
FIG. 19 is a perspective view of a wrist according to another embodiment of the invention.
Figure 20:
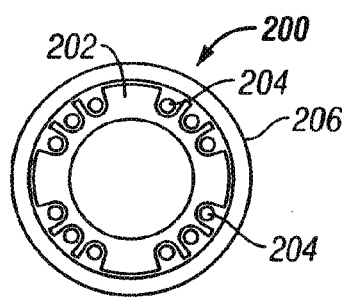
FIG. 20 is a plan view of a wrist according to another embodiment of the invention.

FIG. 19 shows a wrist 190 including a plurality of disks 192 supported by alternating beams or ribs 194, 196 oriented in orthogonal directions to facilitate pitch and yaw bending of the wrist 190. The wrist 190 may be formed from a tube by removing cut-outs between adjacent disks 192 to leave alternating layers of generally orthogonal ribs 194, 196 between the adjacent disks 192. The disks 192 have holes 198 for actuation cables to pass therethrough. The disks 192 and ribs 194, 196 may be made of a variety of material such as steel, aluminum, nitinol, or plastic. In an alternate embodiment of the wrist 200 as illustrated in FIG. 20, the disks 202 include slots 204 instead of holes for receiving the cables. Such a tube is easier to extrude than a tube with holes for passing through cables. A spring 206 is wound over the disks 202 to support the cables.

Figure 21:
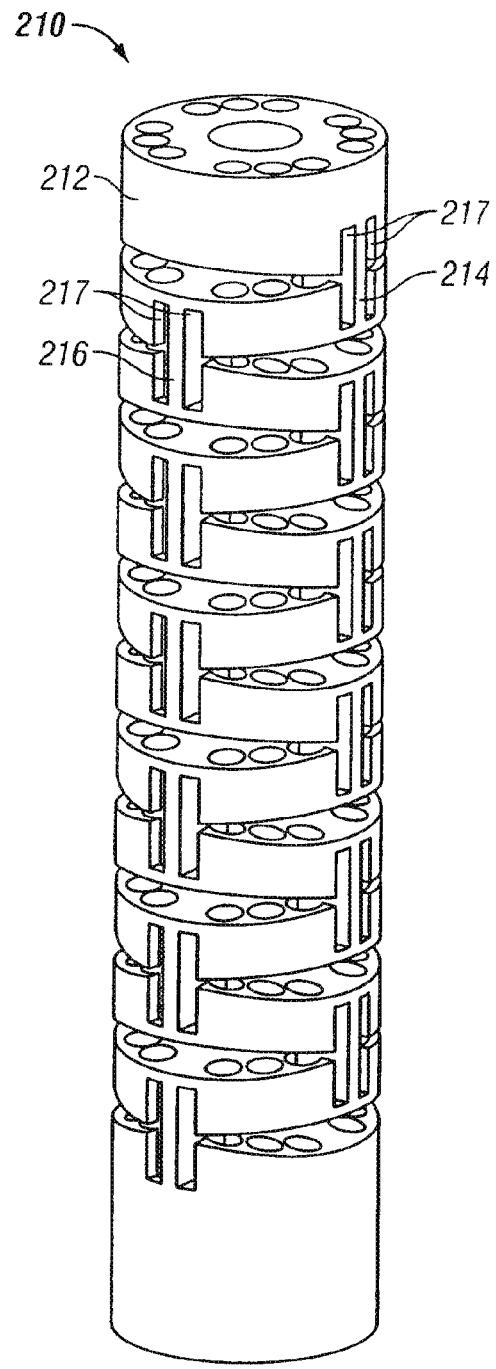
FIG. 21 is a perspective view of a wrist according to another embodiment of the invention.

In FIG. 21, the wrist 210 includes disks 212 supported by alternating beams or ribs 214, 216 having cuts or slits 217 on both sides of the ribs into the disks 212 to make the ribs 214, 216 longer than the spacing between the disks 212. This configuration may facilitate bending with a smaller radius of curvature than that of the wrist 190 in FIG. 19 for the same wrist length, or achieve the same radius of curvature using a shorter wrist. A bending angle of about 15 degrees between adjacent disks 212 is typical in these embodiments. The disks 212 have holes 218 for receiving actuation cables.

I. Wrist Employing Thin Disks Distributed Along Coil Spring

Figure 23:
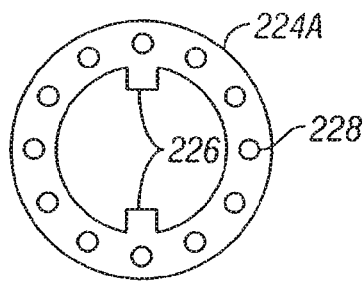
FIGS. 23 and 24 are plan views of the disks in the wrist of FIG. 22.
Figure 24:
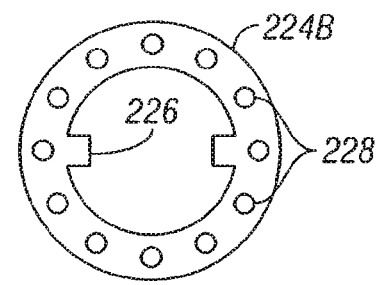
Figure 25:
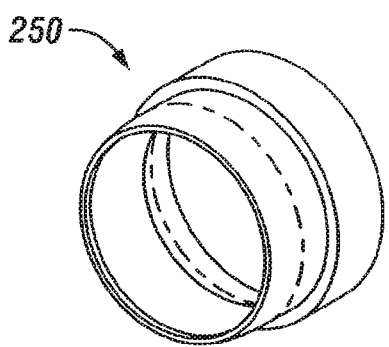
FIG. 25 is a perspective view of an outer piece for the wrist of FIG. 22.
Figure 26:
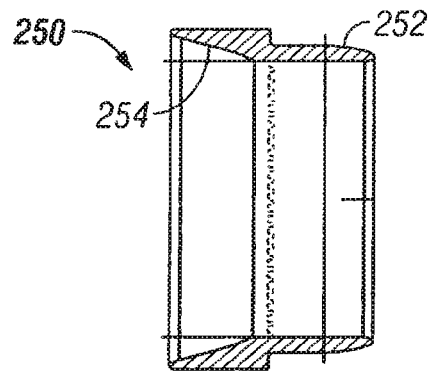
FIG. 26 is a cross-sectional view of the outer piece of FIG. 25.

FIG. 22 shows a portion of a wrist 220 including a coil spring 222 with a plurality of thin disks 224 distributed along the length of the spring 222. Only two disks 224 are seen in the wrist portion of FIG. 22, including 224A and 224B which are oriented with tabs 226 that are orthogonal to each other, as illustrated in FIGS. 23 and 24. The spring 222 coils at solid height except for gaps which are provided for inserting the disks 224 therein. The spring 222 is connected to the disks 224 near the inner edge and the tabs 226 of the disks 224. The disks 224 may be formed by etching, and include holes 228 for receiving actuation cables. The tabs 226 act as the fulcrum to allow the spring 222 to bend at certain points during bending of the wrist 220 in pitch and yaw. The disks 224 may be relatively rigid in some embodiments, but may be flexible enough to bend and act as spring elements during bending of the wrist 220 in other embodiments. A silicone outer cover may be provided around the coil spring 222 and disks 224 as a dielectric insulator. In addition, the spring 222 and disks 224 assembly may be protected by an outer structure formed, for example, from outer pieces or armor pieces 250 FIGS. 25 and 26. Each armor piece 250 includes an outer mating surface 252 and an inner mating surface 254. The outer mating surface 252 of one armor piece 250 mates with the inner mating surface 254 of an adjacent armor piece 250. The armor pieces 250 are stacked along the length of the spring 222, and maintain contact as they rotate from the bending of the wrist 220.

J. Wrist Having Outer Braided Wires

The flexible wrist depends upon the stiffness of the various materials relative to the applied loads for accuracy. That is, the stiffer the materials used and/or the shorter the length of the wrist and/or the larger diameter the wrist has, the less sideways deflection there will be for the wrist under a given surgical force exerted. If the pulling cables have negligible compliance, the angle of the end of the wrist can be determined accurately, but there can be a wandering or sideways deflection under a force that is not counteracted by the cables. If the wrist is straight and such a force is exerted, for example, the wrist may take on an S-shape deflection. One way to counteract this is with suitable materials of sufficient stiffness and appropriate geometry for the wrist. Another way is to have half of the pulling cables terminate halfway along the length of the wrist and be pulled half as far as the remaining cables, as described in U.S. patent application Ser. No. 10/187,248. Greater resistance to the S-shape deflection comes at the expense of the ability to withstand moments. Yet another way to avoid the S-shape deflection is to provide a braided cover on the outside of the wrist.

FIG. 27 shows a wrist 270 having a tube 272 that is wrapped in outer wires 274. The wires 274 are each wound to cover about 360 degree rotation between the ends of the tube 272. To increase the torsional stiffness of the wrist 270 and avoid S-shape deflection of the wrist 270, the outer wires 274 can be wound to form a braided covering over the tube 272. To form the braided covering, two sets of wires including a right-handed set and a left-handed set (i.e., one clockwise and one counter-clockwise) are interwoven. The weaving or plaiting prevents the clockwise and counterclockwise wires from moving radially relative to each other. The torsional stiffness is created, for example, because under twisting, one set of wires will want to grow in diameter while the other set shrinks. The braiding prevents one set from being different from the other, and the torsional deflection is resisted. It is desirable to make the lay length of the outer wires 274 equal to the length of the wrist 270 so that each individual wire of the braid does not have to increase in length as the wrist 270 bends in a circular arc, although the outer wires 274 will need to slide axially. The braid will resist S-shape deflection of the wrist 270 because it would require the outer wires 274 to increase in length. Moreover, the braid may also protect the wrist from being gouged or cut acting as armor. If the braided cover is non-conductive, it may be the outermost layer and act as an armor of the wrist 270. Increased torsional stiffness and avoidance of S-shape deflection of the wrist can also be accomplished by layered springs starting with a right hand wind that is covered by a left hand wind and then another right hand wind. The springs would not be interwoven.

K. Wrist Cover

The above discloses some armors or covers for the wrists. FIGS. 28 and 29 show additional examples of wrist covers. In FIG. 28, the wrist cover 280 is formed by a flat spiral of non-conductive material, such as plastic or ceramic. When the wrist is bent, the different coils of the spiral cover 280 slide over each other. FIG. 29 shows a wrist cover 290 that includes bent or curled edges 292 to ensure overlap between adjacent layers of the spiral. To provide torsional stiffness to the wrist, the wrist cover 300 may include ridges or grooves 302 oriented parallel to the axis of the wrist. The ridges 302 act as a spline from one spiral layer to the next, and constitute a torsional stabilizer for the wrist. Add discussion of nitinol laser cover configured like stents.

The above-described arrangements of apparatus and methods are merely illustrative of applications of the principles of this invention and many other embodiments and modifications may be made without departing from the spirit and scope of the invention as defined in the claims. The scope of the invention should, therefore, be determined not with reference to the above description, but instead should be determined with reference to the appended claims along with their full scope of equivalents.

What is claimed is:

1. A minimally invasive surgical instrument comprising:
   an elongate shaft having a working end, a proximal end, and a shaft axis between the working end and the proximal end;
   an end effector;
   a wrist member having a flexible tube including an axis extending through an interior surrounded by a wall, the wall of the flexible tube including a plurality of lumens oriented generally parallel to the axis of the flexible tube, the wrist member having a proximal portion connected to the working end of the elongate shaft and a distal portion connected to the end effector; and a plurality of actuation cables having distal portions connected to the end effector and extending from the distal portion through the lumens of the wall of the wrist member toward the elongate shaft to proximal portions which are actuatable to bend the wrist member in pitch rotation and yaw rotation;

wherein the flexible tube comprises an inner diameter and an outer diameter, the wall of the flexible tube including a plurality of slots adjacent the inner diameter to form the lumens at the slots.

2. The instrument of claim 1 wherein the wall of the flexible tube includes twelve lumens.

3. The instrument of claim 1 wherein the outer cover comprises a high modulus material.

4. The instrument of claim 1 wherein the flexible tube comprises a plurality of springs each disposed around one of the plurality of slots.

5. The instrument of claim 1 further comprising an inner spring disposed around the interior of the flexible tube.

6. The instrument of claim 1 wherein the wall of the flexible tube comprises a plurality of axial sliding members which are slidably connected with each other by an axial connection generally parallel to the axis of the flexible tube.

7. The instrument of claim 6 wherein the axial connection comprises a tongue and groove connection.

8. The instrument of claim 6 wherein each axial sliding member includes a lumen for receiving one of the actuation cables.

9. The instrument of claim 6 wherein each axial sliding member is integrally formed with one of the actuation cables as an integrated sliding element.

10. The instrument of claim 1 wherein the wrist includes a distal termination disk connected to a distal end of the flexible tube, the distal termination disk being substantially more rigid than the flexible tube.

11. A minimally invasive surgical instrument comprising:
an elongate shaft having a working end, a proximal end, and a shaft axis between the working end and the proximal end;
an end effector;
a wrist member having a flexible tube comprising an inner diameter and an outer diameter, a wall of the flexible tube adjacent the inner diameter including a plurality of lumens oriented generally parallel to the axis of the flexible tube, the wrist member having a proximal portion connected to the working end of the elongate shaft and a distal portion connected to the end effector; and
a plurality of actuation cables having distal portions connected to the end effector and extending from the distal portion through the lumens of the wall of the wrist member toward the elongate shaft to proximal portions which are actuatable to bend the wrist member in pitch rotation and yaw rotation;
wherein each actuation cable is looped around a distal portion of the wall of the flexible tube to extend through two adjacent lumens.

12. A minimally invasive surgical instrument comprising:
an elongate shaft having a working end, a proximal end, and a shaft axis between the working end and the proximal end;
an end effector;
a wrist member having a flexible tube comprising an inner diameter and an outer diameter, a wall of the flexible tube adjacent the inner diameter including a plurality of lumens oriented generally parallel to the axis of the flexible tube, the wrist member having a proximal portion connected to the working end of the elongate shaft and a distal portion connected to the end effector; and
a plurality of actuation cables having distal portions connected to the end effector and extending from the distal portion through the lumens of the wall of the wrist member toward the elongate shaft to proximal portions which are actuatable to bend the wrist member in pitch rotation and yaw rotation;
wherein the flexible tube includes a plurality of transverse cut-outs alternating orthogonally relative to each other.

13. The instrument of claim 12 further comprising an outer cover wrapped around an external surface of the flexible tube.

14. The instrument of claim 12 wherein the transverse cut-outs comprise alternating layers of cut-outs each having a pair of cut-outs which are disposed opposite to one another, the cut-outs of each layer being oriented in a direction which is spaced by about 90 degrees from the cut-outs of an adjacent layer.

15. The instrument of claim 14 wherein the transverse cut-outs leave ribs connected between disk portions above and below the ribs, and wherein slits extending generally along the axis of the flexible tube into the disk portions are provided on both sides of the ribs.

16. A minimally invasive surgical instrument comprising:
an elongate shaft having a working end, a proximal end, and a shaft axis between the working end and the proximal end;
an end effector;
a wrist member having a flexible tube comprising an inner diameter and an outer diameter, a wall of the flexible tube adjacent the inner diameter including a plurality of lumens oriented generally parallel to the axis of the flexible tube, the wrist member having a proximal portion connected to the working end of the elongate shaft and a distal portion connected to the end effector; and
a plurality of actuation cables having distal portions connected to the end effector and extending from the distal portion through the lumens of the wall of the wrist member toward the elongate shaft to proximal portions which are actuatable to bend the wrist member in pitch rotation and yaw rotation;
further comprising a braided cover on an exterior surface of the flexible tube, the braided cover having a first set of wires wound in a clockwise direction between a proximal end and a distal end of the flexible tube and a second set of wires wound in a counter-clockwise direction between the proximal end and the distal end of the flexible tube and interwoven with the first set of wires.

17. A minimally invasive surgical instrument comprising:
an elongate shaft having a working end, a proximal end, and a shaft axis between the working end and the proximal end;
an end effector;
a wrist member having a flexible tube comprising an inner diameter and an outer diameter, a wall of the flexible tube adjacent the inner diameter including a plurality of lumens oriented generally parallel to the axis of the flexible tube, the wrist member having a proximal portion connected to the working end of the elongate shaft and a distal portion connected to the end effector; and
a plurality of actuation cables having distal portions connected to the end effector and extending from the distal portion through the lumens of the wall of the wrist member toward the elongate shaft to proximal portions which are actuatable to bend the wrist member in pitch rotation and yaw rotation;

wherein the flexible tube comprises a plurality of axial springs coupled with each other and disposed around a circumference of the flexible tube, each axial spring having coils which overlap with coils of an adjacent axial spring to provide one of the lumens for receiving one of the actuation cables.

18. A minimally invasive surgical instrument comprising:

an elongate shaft having a working end, a proximal end, and a shaft axis between the working end and the proximal end;

an end effector;

a wrist member having a flexible tube comprising an inner diameter and an outer diameter, a wall of the flexible tube adjacent the inner diameter including a plurality of lumens oriented generally parallel to the axis of the flexible tube, the wrist member having a proximal portion connected to the working end of the elongate shaft and a distal portion connected to the end effector; and a plurality of actuation cables having distal portions connected to the end effector and extending from the distal portion through the lumens of the wall of the wrist member toward the elongate shaft to proximal portions which are actuatable to bend the wrist member in pitch rotation and yaw rotation;

wherein the flexible tube comprises a wave spring having a plurality of wave spring segments which include high points and low points connected in series along the axis of the flexible tube, the high points of one wave spring segment being connected to the low points of an adjacent wave spring segment.

* * * * *